(12) United States Patent
Adler et al.

(10) Patent No.: US 8,928,671 B2
(45) Date of Patent: Jan. 6, 2015

(54) RECORDING AND ANALYZING DATA ON A 3D AVATAR

(75) Inventors: B. Thomas Adler, Sunnyvale, CA (US);
David Marvit, San Francisco, CA (US);
Jawahar Jain, Los Altos, CA (US)

(73) Assignee: Fujitsu Limited, Kawasaki-shi (JP)

( * ) Notice: Subject to any disclaimer, the term of this patent is extended or adjusted under 35 U.S.C. 154(b) by 33 days.

(21) Appl. No.: 12/954,441

(22) Filed: Nov. 24, 2010

(65) Prior Publication Data

US 2012/0127157 A1   May 24, 2012

(51) Int. Cl.
| G06T 15/00 | (2011.01) |
|---|---|
| G06F 19/00 | (2011.01) |
| A61B 5/00 | (2006.01) |
| A61B 5/08 | (2006.01) |
| G06Q 10/00 | (2012.01) |
| G06Q 50/24 | (2012.01) |
| A61B 5/091 | (2006.01) |
| A61B 5/11 | (2006.01) |
| A61B 5/1455 | (2006.01) |
| A61B 5/16 | (2006.01) |

(52) U.S. Cl.
CPC .......... *G06F 19/3418* (2013.01); *A61B 5/0022* (2013.01); *A61B 5/0024* (2013.01); *A61B 5/08* (2013.01); *A61B 5/0816* (2013.01); *A61B 5/091* (2013.01); *A61B 5/1118* (2013.01); *A61B 5/1121* (2013.01); *A61B 5/14551* (2013.01); *A61B 5/165* (2013.01); *A61B 5/4803* (2013.01); *A61B 5/744* (2013.01); *A61B 2562/0219* (2013.01); *G06F 19/322* (2013.01); *G06F 19/3437* (2013.01); *G06F 19/345* (2013.01);
*G06F 19/363* (2013.01); *G06Q 10/00* (2013.01); *G06Q 50/24* (2013.01)
USPC ........... 345/473; 345/474; 345/475; 600/301; 600/547; 600/549

(58) Field of Classification Search
CPC .................................................... G06F 19/3437
USPC ........... 345/473, 474, 475; 600/301, 547, 549
See application file for complete search history.

(56) References Cited

U.S. PATENT DOCUMENTS

| 4,823,807 A | 4/1989 | Russell |
|---|---|---|
| 5,367,454 A | 11/1994 | Kawamoto |
| 5,662,118 A | 9/1997 | Skubick |
| 5,964,701 A | 10/1999 | Asada |

(Continued)

FOREIGN PATENT DOCUMENTS

| WO | WO 2006/090371 | 8/2006 |
|---|---|---|
| WO | WO 2006/090371 A2 | 8/2006 |
| WO | WO 2006/119186 | 11/2006 |

OTHER PUBLICATIONS

U.S. Appl. No. 13/018,004, filed Jan. 31, 2011, Jawahar Jain.

(Continued)

*Primary Examiner* — Phu K Nguyen
(74) *Attorney, Agent, or Firm* — Baker Botts L.L.P.

(57) ABSTRACT

In particular embodiments, a method includes generating a 3D display of an avatar of a person, where the avatar can receive inputs identifying a type of a physiological event, a location of the physiological event in or on a person's body in three spatial dimensions, a time range of the physiological event, a quality of the physiological event, and rendering the physiological event on the avatar based on the inputs.

35 Claims, 9 Drawing Sheets

(56) References Cited

U.S. PATENT DOCUMENTS

| | | | |
|---|---|---|---|
| 6,026,322 A * | 2/2000 | Korenman et al. | 600/547 |
| 6,185,451 B1 | 2/2001 | Richardson et al. | |
| 6,440,069 B1 | 8/2002 | Raymond | |
| 6,595,929 B2 * | 7/2003 | Stivoric et al. | 600/549 |
| 6,678,549 B2 | 1/2004 | Cusimano et al. | |
| 6,690,397 B1 * | 2/2004 | Daignault, Jr. | 715/764 |
| 7,273,454 B2 | 9/2007 | Raymond | |
| 7,297,119 B2 | 11/2007 | Westbrook | |
| 7,499,048 B2 * | 3/2009 | Sieracki et al. | 345/419 |
| 7,596,503 B2 | 9/2009 | Ben-Attar et al. | |
| 7,671,874 B2 * | 3/2010 | Daignault, Jr. | 345/619 |
| 7,691,067 B2 | 4/2010 | Westbrook | |
| 7,856,360 B2 | 12/2010 | Kramer | |
| 7,928,995 B2 * | 4/2011 | Daignault, Jr. | 345/619 |
| 7,964,390 B2 | 6/2011 | Rozakis | |
| 8,046,241 B1 * | 10/2011 | Dodson | 705/2 |
| 8,126,542 B2 | 2/2012 | Grey | |
| 8,187,201 B2 | 5/2012 | Lynn | |
| 8,311,848 B2 * | 11/2012 | Subash et al. | 705/2 |
| 2003/0117651 A1 | 6/2003 | Matraszek et al. | |
| 2003/0208113 A1 | 11/2003 | Mault | |
| 2004/0122296 A1 | 6/2004 | Hatlestad et al. | |
| 2004/0152961 A1 | 8/2004 | Carlson | |
| 2005/0015115 A1 | 1/2005 | Sullivan | |
| 2005/0119586 A1 | 6/2005 | Coyle | |
| 2006/0173259 A1 | 8/2006 | Flaherty et al. | |
| 2006/0189899 A1 | 8/2006 | Flaherty et al. | |
| 2006/0293602 A1 | 12/2006 | Clark | |
| 2007/0060803 A1 | 3/2007 | Liljeryd | |
| 2007/0073169 A1 | 3/2007 | Averina | |
| 2007/0073181 A1 | 3/2007 | Pu | |
| 2007/0167867 A1 | 7/2007 | Wolf | |
| 2007/0276270 A1 | 11/2007 | Tran | |
| 2008/0019299 A1 | 1/2008 | Lekutai | |
| 2008/0146893 A1 | 6/2008 | Levendowski | |
| 2008/0154098 A1 | 6/2008 | Morris | |
| 2008/0167535 A1 * | 7/2008 | Stivoric et al. | 600/301 |
| 2008/0195980 A1 | 8/2008 | Morris | |
| 2008/0208015 A1 | 8/2008 | Morris | |
| 2008/0214903 A1 | 9/2008 | Orbach | |
| 2008/0281550 A1 | 11/2008 | Hogle | |
| 2009/0182206 A1 | 7/2009 | Najafi | |
| 2010/0145219 A1 | 6/2010 | Grey | |
| 2011/0106011 A1 | 5/2011 | Cinar | |
| 2011/0125063 A1 | 5/2011 | Shalon et al. | |
| 2011/0224498 A1 | 9/2011 | Banet | |
| 2012/0190992 A1 | 7/2012 | Liao et al. | |

OTHER PUBLICATIONS

U.S. Appl. No. 12/954,441, filed Nov. 24, 2010, B. Thomas Adler.
U.S. Appl. No. 13/018,071, filed Jan. 31, 2011, Jawahar Jain.
U.S. Appl. No. 12/954,251, filed Nov. 24, 2010, Jawahar Jain.
U.S. Appl. No. 12/954,302, filed Nov. 24, 2010, Jawahar Jain.
U.S. Appl. No. 12/954,398, filed Nov. 24, 2010, Stergios Stergiou.
Bottorff, Michael, "Safety and Statins: Pharmacologic and Clinical Perspectives," *Preventive Medicine in Managed Care*, 4:2, Sup., S30-S37, Nov. 2004.
Copeland, Michael, "The Ultimate Personal Technology," *Fortune Magazine on CNN Money.com*, http://tech.fortune.cnn.com/2010/04/21/the-ultimate-personal-technology/ downloaded May 24, 2010, Apr. 21, 2010.
Hippisley-Cox, Julia et al., "Unintended effects of statins in men and women in England and Wales: population based cohort study using the QResearch database," *BMJ 2010*;340:c2197 doi:10.1136/bmj.c2197, 2010.
"How Pharmacists and the Internet Improved Hypertension Control," *Wall Street Journal Health Blog*, http://blogs.wsj.com/health/2010/05/21/how-pharmacists-and-the-internet-improved-hyper . . . downloaded May 21, 2010.
Lohr, Steve, "High-Tech Alternatives to High-Cost Care," http://www.nytimes.com/2010/05/23/business/23unboxed.html downloaded May 24, 2010.
"Myotrac 60Hz," Futurehealth.org *Product Description*, http://www.futurehealth.org/populum/pageproduct.php?f=Myotrac-60Hz-051408-98.html downloaded Nov. 2, 2010.
Mohaupt, Markus G. et al., "Association Between Statin-Associated Myopathy and Skeletal Muscle Damage", CMAJ, Canadian Medical Association, pp. E11-E18, Jul. 7, 2009.
"Surface EMG Sensors," Delsys Product Description, http://www.delsys.com/products/emgsensors.html downloaded on Nov. 2, 2010, 2008.
Thompson, Paul et al., "Statin Associated Myopathy," *JAMA*, 289(13), downloaded www.jama.com on Jun. 30, 2010, Apr. 2, 2003.
Trudeau, Michelle, "Mobile Phone App: 'Therapist in Your Pocket,'" *89.3 KPCC Southern California Public Radio*, downloaded http://www.scpr.org/news/2010/05/23/mobile-phone-app-therapist-your-pocket/ on Jun. 15, 2010.
Wolf, Gary, "Measuring Mood—Current Research and New Ideas," *The Quantified Self*, http://www.kk.org/quantifiedself/2009/02/measuring-mood—current-resea.php downloaded May 15, 2010, Feb. 2009.
Wolf, Gary, "Tracking Mood—The Dream of a Mood Phone," *The Quantified Self*, http://www.kk.org/quantifiedself/2009/01/tracking-mood—the-dream-of-a.php downloaded Jun. 15, 2010, Jan. 2009.
EMG Sensors, "Surface EMG Sensors", http://www.delsys.com/products/emgsensors.html, downloaded Nov. 2, 2010, 2008.
Futurehealth—Product: Myotrac 60Hz, "Myotrac 60Hz", http://www.futurehealth.org/populum/pageproduct.php?f=Myotrac-60Hz-051408.html, downloaded Nov. 2, 2010, 2002.
Ruchi Mathur, MD, FRCP ©, "Insulin Resistance Symptoms, Causes, and Treatment on MedicineNet.com", http://www.medicinenet.com/script/main/art.asp?articlekey=30653&pf=3&page=1, downloaded Jul. 2, 2010, Mar. 30, 2009.
Walter Morgan, M.D. and Heidi L. Hodge, M.D., "Diagnostic Evaluation of Dyspnea", AAFP American Family Physician, http://www.aafp.org/afp/980215ap/morgan.html, downloaded Jun. 29, 2010, Feb. 15, 1998.
Margaret E. Morris, "Technologies for Heart and Mind: New Directions in Embedded Assessment", Intel Technology Journal, vol. 11, Issue 01, ISSN 1535-864X DOI: 11.1535/ltj.1101.07, Feb. 15, 2007.
EMC Sensors, NEXGEN Ergonomics"The Global Source for Software & Instrumentation for Ergonomics, Biomechanics & Medicine", http://www.nexgenergo.com/medical/biodatamg.html, downloaded Nov. 2, 2010, 1997.
Vaskar Mukerji, "Dyspnea, Orthopnea, and Paroxysmal Nocturnal Dyspnea", Chapter 11, Clinical Methods: The History, Physical, and Laboratory Examinations. 3rd edition, 1990, Butterworth Publishers, a division of Reed Publishing, 1990.
U.S. Department of Health and Human Services, National Institute of Health, "Insulin Resistance and Pre-Diabetes", NH Publication No. 09-4893, Oct. 2008.
Wolf, Gary, "The Data-Driven Life", The New Your Times, Magazing Preview, NYTimes.com, http://www.nytimes.com/2010/05/02/magazine/02self-measurement-t.html?hp=&pagewan . . . , downloaded Apr. 29, 2010, Apr. 26, 2010.
Ruisinger, Janelle F, PharmD et al., "Once-a-Week Rosuvastatin (2.5 to 20 mg) in Patients With a Previous Statin Intolerance", The American Journal of Cardiology, vol. 103, Issue 3, pp. 393-394, Nov. 21, 2008.
Bonato, P., "Wearable Sensors and Systems. From Enabling Technololgy to Clinical Applications", IEEE Eng Med Bio Mag, http://www.seeingwithsound.com/newpubs/wearablesensors/, downloaded Nov. 2, 2010, May-Jun. 2010.
"Dyspnea", Wikipedia.com., http://en.wikipedia.org/wiki/Dyspnea, Nov. 2010.
"Glycated Hemoglobin", Wikipedia.com, http://en.wikipedia.org/wiki/Glycated_hemoglobin, Nov. 2010.
"Insulin Resistance", Wikipedia.com, http://en.wikipedia.org/wiki/Insulin_resistance, Nov. 2010.
"Myopathy", Wikipedia.com, http://en.wikipedia.org/wiki/Myopathy, Nov. 2010.
"Sleep Apnea", Wikipedia.com, http://en.wikipedia.org/wiki/Sleep_apnea, Nov. 2010.
"Statin", Wikipedia.com, http://en.wikipedia.org/wiki/Statin, Nov. 2010.

(56) References Cited

OTHER PUBLICATIONS

Mair, G., et al., "Airway dimensions in COPD: Relationships with clinical variables," Respitory Medicine 104, 1683-1690, 2010.
Search Report for EP 11189410, Feb. 23, 2012.
Search Report for EP 11188869.9, Feb. 23, 2012.
Search Report for EP 11189871, Mar. 1, 2012.
Search Report for DE 102008023328, Nov. 19, 2009.
Search Report for WO 02073503, Sep. 19, 2002.
Search Report for WO 2010107980, Sep. 23, 2010.
Search Report for WO 2011005633, Jan. 13, 2011.
Search Report for WO 2008062099, May 29, 2008.
J. Jain, U.S. Appl. No. 12/954,302, Final Office Action from U.S. Patent and Trademark Office, Jul. 24, 2013.
S. Stergiou, U.S. Appl. No. 12/954,398, Final Office Action from U.S. Patent and Trademark Office, Jul. 17, 2013.
Communication pursuant to Article 94(3) EPC from European Patent Office dated Jul. 22, 2013 regarding Application No. 11 188 869 9-1958 (6 pages).
Communication pursuant to Article 94(3) EPC from European Patent Office regarding Application No. 11 189 410.1-1657 (4 pages), Sep. 16, 2013.
EPO Examination Report for EP 11189766.6, Jan. 3, 2013.
EPO Examination Report for EP 11190166.6, Nov. 25, 2013.
Huang, M., *Resilience in Chronic Disease*, Queensland University of Technology, Institute of Health and Biomedical Innovation, School of Nursing and Midwifery, 324 pgs, 2009.
Qi, D. et al. *Glucocorticoids produce whole body insulin resistance with changes in cardiac metabolism*, http://www.ajpendo-physiology.org, 15 pgs, Jun. 21, 2012.
Qi et al., "Glucocorticoids produce whole body insulin resistance with changes in cardiac metabolism," Oct. 31, 2006.
EPO Communication transmitting the extended European search report dated Oct. 23, 2012, received from the foreign associate on Nov. 19, 2012, regarding P118010EP00/TCS, Application No. 11189766.6-2201/2479692.
EPO Communication pursuant to Article 94(3) EPC, Appln. No. 11 190 166.6-1265 dated Jan. 3, 2013.
J. Jain, U.S. Appl. No. 12/954,035, Response to Non-final Rejection, May 24, 2012.
J. Jain, U.S. Appl. No. 12/954,035, Final Rejection, US Patent and Trademark Office, Sep. 24, 2012.
J. Jain, U.S. Appl. No. 12/954,035, Response to Final Rejection, Nov. 14, 2012.
J. Jain, U.S. Appl. No. 12/954,035, Request for Continued Examination and Amendment, Jan. 24, 2013.
J. Jain, U.S. Appl. No. 13/018,004, Request for Election Restriction, US Patent and Trademark Office, Sep. 17, 2012.
J. Jain, U.S. Appl. No. 13/018,004, Response to Election Restriction, Oct. 15, 2012.
J. Jain, U.S. Appl. No. 13/018,071, Request for Election Restriction, US Patent and Trademark Office, Mar. 21, 2012.
J. Jain, U.S. Appl. No. 13/018,071, Response to Election Restriction, Apr. 6, 2012.
J. Jain, U.S. Appl. No. 13/018,071, Non-final Rejection, US Patent and Trademark Office, Jun. 21, 2012.
J. Jain, U.S. Appl. No. 13/018,071, Response to Non-final Rejection, Sep. 14, 2012.
J. Jain, U.S. Appl. No. 12/954,302, Non-final Rejection, US Patent and Trademark Office, Jan. 4, 2013.
S. Stergiou, U.S. Appl. No. 12/954,398, Non-final Rejection, US Patent and Trademark Office, Dec. 5, 2012.
Min-Feng Huang, "Resilience in chronic disease: The relationship among risk factors, protective factors, adaptive outcomes, and the level of resilience in adults with diabetes," 2009, Queensland University of Technology, Institute of Health and Biomedical Innovation School of Nursing and Midwifery, pp. 1-310, 2009.
Jain, U.S. Appl. No. 13/018,004, Non-final Office Action from US PTO, Jun. 12, 2013.
Jain, U.S. Appl. No. 13/018,071, Non-final Office Action from US PTO, Jun. 13, 2013.
Jain, U.S. Appl. No. 12/954,251, Non-final Office Action from US PTO, Dec. 21, 2012.
Jain, U.S. Appl. No. 12/954,251, Response to Non-final Office Action, Mar. 19, 2013.
Jain, U.S. Appl. No. 12/954,251, Final Office Action from US PTO, Apr. 2, 2013.
Jain, U.S. Appl. No. 12/954,251, Response to Final Office Action, May 10, 2013.
Jain, U.S. Appl. No. 12/954,302, Response to Non-final Office Action, Apr. 4, 2013.
Stergiou, U.S. Appl. No. 12/954,398, Response to Non-final Office Action, Mar. 4, 2013.
EPO 11188869.9 Summons, Jun. 25, 2014.
International Publication WO2010/064237 A1, Jun. 10, 2010.
J. Van Meeteren XP008168986, Jun. 6, 2006.
Examination Report 11190166.6-1657, Jun. 3, 2014.

\* cited by examiner

RECORDING AND ANALYZING DATA ON A 3D AVATAR

TECHNICAL FIELD

This disclosure generally relates to sensors and sensor networks for monitoring and analyzing a person's health.

BACKGROUND

A sensor typically measures a physical quantity and converts it into a signal that an observer or an instrument can read. For example, a mercury-in-glass thermometer converts a measured temperature into expansion and contraction of a liquid that can be read on a calibrated glass tube. A thermocouple converts temperature to an output voltage that a voltmeter can read. For accuracy, sensors are generally calibrated against known standards.

A sensor's sensitivity indicates how much the sensor's output changes when the measured quantity changes. For instance, if the mercury in a thermometer moves 1 cm when the temperature changes by 1° C., the sensitivity is 1 cm/° C. Sensors that measure very small changes have very high sensitivities. Sensors may also have an impact on what they measure; for instance, a room temperature thermometer inserted into a hot cup of liquid cools the liquid while the liquid heats the thermometer. The resolution of a sensor is the smallest change it can detect in the quantity that it is measuring. The resolution is related to the precision with which the measurement is made.

The output signal of a sensor is typically linearly proportional to the value or simple function (logarithmic) of the measured property. The sensitivity is then defined as the ratio between output signal and measured property. For example, if a sensor measures temperature and has a voltage output, the sensitivity is a constant with the unit [V/K]; this sensor is linear because the ratio is constant at all points of measurement.

BRIEF DESCRIPTION OF THE DRAWINGS

FIG. 8 illustrates an example user-input sensor for collecting information of a physiological event on a three-dimensional representation of a person's body.

DESCRIPTION OF EXAMPLE EMBODIMENTS

Figure 1:
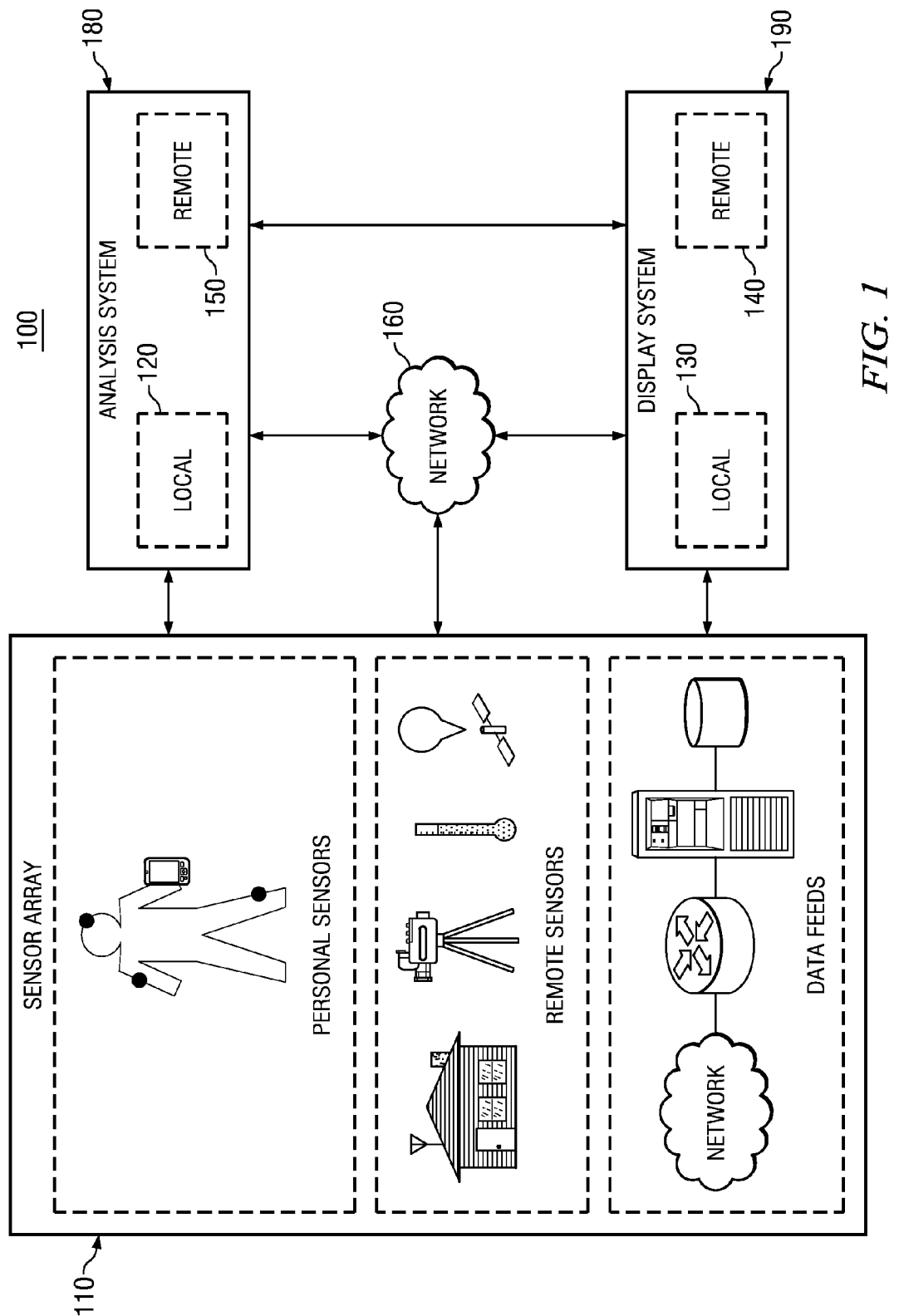
FIG. 1 illustrates an example sensor network.

FIG. 1 illustrates an example sensor network 100. Sensor network 100 comprises sensor array 110, analysis system 180, and display system 190. The components of sensor network 100 may be connected to each other in any suitable configuration, using any suitable type of connection. The components may be connected directly or over a network 160, which may be any suitable network (e.g., the internet).

Sensor network 100 enables the collecting, processing, sharing, and visualizing, displaying, archiving, and searching of sensor data. The data collected by sensor array 110 may be processed, analyzed, and stored using the computational and data storage resources of sensor network 100. This may be done with both centralized and distributed computational and storage resources. Sensor network 100 may integrate heterogeneous sensor, data, and computational resources deployed over a wide area. Sensor network 100 may be used to undertake a variety of tasks, such as physiological, psychological, behavioral, and environmental monitoring and analysis.

Sensor array 110 comprises one or more sensors. A sensor receives a stimulus and converts it into a data stream. The sensors in sensor array 110 may be of the same type (e.g., multiple thermometers) or various types (e.g., a thermometer, a barometer, and an altimeter). Sensor array 110 may transmit one or more data streams based on the one or more stimuli to one or more analysis systems 180 over any suitable network. In particular embodiments, a sensor's embedded processors may perform certain computational activities (e.g., image and signal processing) that could also be performed by analysis system 180.

As used herein, a sensor in sensor array 110 is described with respect to a user. Therefore, a sensor may be personal or remote with respect to the user. Personal sensors receive stimulus that is from or related to the user. Personal sensors may include, for example, sensors that are affixed to or carried by the user (e.g., a heart-rate monitor, a input by the user into a smartphone), sensors that are proximate to the user (e.g., a thermometer in the room where the user is located), or sensors that are otherwise related to the user (e.g., GPS position of the user, a medical report by the user's doctor, a user's email inbox). Remote sensors receive stimulus that is external to or not directly related to the user. Remote sensors may include, for example, environmental sensors (e.g., weather balloons, stock market ticker), network data feeds (e.g., news feeds), or sensors that are otherwise related to external information. A sensor may be both personal and remote depending on the circumstances. For example, a thermometer in a user's home may be considered personal while the user is at home, but remote when the user is away from home.

Analysis system 180 may monitor, store, and analyze one or more data streams from sensor array 110. Analysis system 180 may have subcomponents that are local 120, remote 150, or both. Display system 190 may render, visualize, display, message, notify, and publish to one or more users or systems based on the output of analysis system 180. Display system 190 may have subcomponents that are local 130, remote 140, or both.

As used herein, the analysis and display components of sensor network 100 are described with respect to a sensor. Therefore, a component may be local or remote with respect to the sensor. Local components (i.e., local analysis system 120, local display system 130) may include components that are built into or proximate to the sensor. For example, a sensor could include an integrated computing system and an LCD monitor that function as local analysis system 120 and local display system 130. Remote components (i.e., remote analysis system 150, remote display system 190) may include components that are external to or independent of the sensor. For example, a sensor could transmit a data stream over a network to a remote server at a medical facility, wherein dedicated computing systems and monitors function as remote analysis system 150 and remote display system 190. In particular embodiments, each sensor in sensor array 110 may utilize either local or remote display and analysis components, or both. In particular embodiments, a user may selectively access, analyze, and display the data streams from one or more sensors in sensor array 110. This may be done, for example, as part of running a specific application or data analysis algorithm. The user could access data from specific types of sensors (e.g., all thermocouple data), from sensors that measure specific types of data (e.g., all environmental sensors), or based on other criteria.

The sensor network embodiments disclosed herein have many possible applications, such as healthcare monitoring of patients, environmental and habitat monitoring, weather monitoring and forecasting, military and homeland security surveillance, tracking of goods and manufacturing processes, safety monitoring of physical structures, and many other uses. Although this disclosure describes particular uses of sensor network 100, this disclosure contemplates any suitable uses of sensor network 100.

Figure 2:
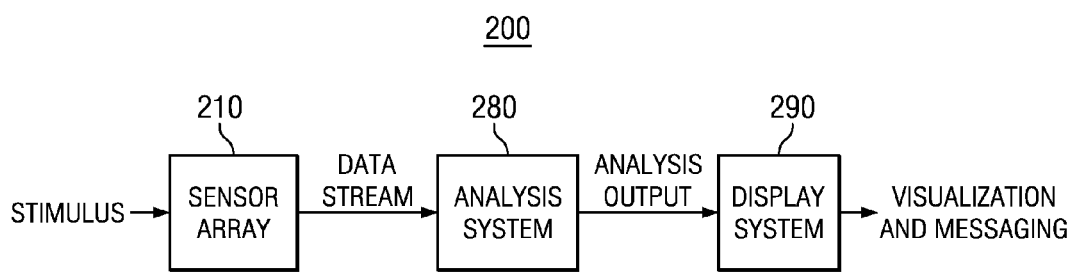
FIG. 2 illustrates an example data flow in a sensor network.

FIG. 2 illustrates an example data flow in a sensor network. In particular embodiments, one or more sensors in a sensor array 210 may receive one or more stimuli. The sensors in sensory array 210 may be of one or more types. The sensor array 210 may transmit one or more data streams based on the one or more stimuli to one or more analysis systems 280 over any suitable network. For example, one sensor could transmit multiple data streams to multiple analysis systems. In another example, multiple sensors could transmit multiple data streams to one analysis system.

In particular embodiments, the sensors in sensor array 210 each produce their own data stream, which is transmitted to analysis system 280. In other embodiments, one or more sensors in sensor array 210 have their output combined into a single data stream.

Analysis system 280 may monitor, store, and analyze one or more data streams. Analysis system 280 may be local, remote, or both. Analysis system 280 may transmit one or more analysis outputs based on the one or more data streams to one or more display systems 290. For example, one analysis system could transmit multiple analysis outputs to multiple display systems. In another example, multiple analysis systems could transmit multiple analysis outputs to one display system.

A display system 290 may render, visualize, display, message, notify, and publish to one or more users based on the one or more analysis outputs. A display system 290 may be local, remote, or both. In particular embodiments, a sensor array 210 could transmit one or more data streams directly to a display system 290. This would allow, for example, display of stimulus readings by the sensor. However, unless context suggests otherwise, this disclosure assumes the data flow illustrated in FIG. 2.

Figure 3:
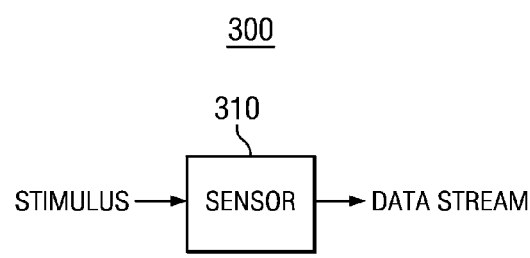
FIG. 3 illustrates an example sensor.

FIG. 3 illustrates an example sensor and data flow to and from the sensor. A sensor 310 is a device which receives and responds to a stimulus. Here, the term "stimulus" means any signal, property, measurement, or quantity that can be detected and measured by a sensor. A sensor responds to a stimulus by generating a data stream corresponding to the stimulus. A data stream may be a digital or analog signal that may be transmitted over any suitable transmission medium and further used in electronic devices. As used herein, the term "sensor" is used broadly to describe any device that receives a stimulus and converts it into a data stream. The present disclosure assumes that the data stream output from a sensor is transmitted to an analysis system, unless otherwise specified.

The sensor 310 includes a stimulus receiving element (i.e., sensing element), a data stream transmission element, and any associate circuitry. Sensors generally are small, battery powered, portable, and equipped with a microprocessor, internal memory for data storage, and a transducer or other component for receiving stimulus. However, a sensor may also be an assay, test, or measurement. A sensor may interface with a personal computer and utilize software to activate the sensor and to view and analyze the collected data. A sensor may also have a local interface device (e.g., keypad, LCD) allowing it to be used as a stand-alone device.

Sensors are able to measure a variety of things, including physiological, psychological, behavioral, and environmental stimulus. Physiological stimulus may include, for example, physical aspects of a person (e.g., stretch, motion of the person, and position of appendages); metabolic aspects of a person (e.g., glucose level, oxygen level, osmolality), biochemical aspects of a person (e.g., enzymes, hormones, neurotransmitters, cytokines), and other aspects of a person related to physical health, disease, and homeostasis. Psychological stimulus may include, for example, emotion, mood, feeling, anxiety, stress, depression, and other psychological or mental states of a person. Behavioral stimulus may include, for example, behavior related a person (e.g., working, socializing, arguing, drinking, resting, driving), behavior related to a group (e.g., marches, protests, mob behavior), and other aspects related to behavior. Environmental stimulus may include, for example, physical aspects of the environment (e.g., light, motion, temperature, magnetic fields, gravity, humidity, vibration, pressure, electrical fields, sound, GPS location), environmental molecules (e.g., toxins, nutrients, pheromones), environmental conditions (e.g., pollen count, weather), other external condition (e.g., traffic conditions, stock market information, news feeds), and other aspects of the environment.

The following is a partial list of sensor types that may be encompassed by various embodiments of the present disclosure: Accelerometer; Affinity electrophoresis; Air flow meter; Air speed indicator; Alarm sensor; Altimeter; Ammeter; Anemometer; Arterial blood gas sensor; Attitude indicator; Barograph; Barometer; Biosensor; Bolometer; Boost gauge; Bourdon gauge; Breathalyzer; calorimeter; Capacitive displacement sensor; Capillary electrophoresis; Carbon dioxide sensor; Carbon monoxide detector; Catalytic bead sensor; Charge-coupled device; Chemical field-effect transistor; Chromatograph; Colorimeter; Compass; Contact image sensor; Current sensor; Depth gauge; DNA microarray; Electrocardiograph (ECG or EKG); Electrochemical gas sensor; Electrolyte-insulator-semiconductor sensor; Electromyograph (EMG); Electronic nose; Electro-optical sensor; Exhaust gas temperature gauge; Fiber optic sensors; Flame detector; Flow sensor; Fluxgate compass; Foot switches; Force sensor; Free fall sensor; Galvanometer; Gardon gauge; Gas detector; Gas meter; Geiger counter; Geophone; Goniometers; Gravimeter; Gyroscope; Hall effect sensor; Hall probe; Heart-rate sensor; Heat flux sensor; High-performance liquid chromatograph (HPLC); Hot filament ionization gauge; Hydrogen sensor; Hydrogen sulfide sensor; Hydrophone; Immunoassay, Inclinometer; Inertial reference unit; Infrared point sensor; Infra-red sensor; Infrared thermometer; Ionization gauge; Ion-selective electrode; Keyboard; Kinesthetic sensors; Laser rangefinder; Leaf electroscope; LED light sensor; Linear encoder; Linear variable differential transformer (LVDT); Liquid capacitive inclinometers; Magnetic anomaly detector; Magnetic compass; Magnetometer; Mass flow sensor; McLeod gauge; Metal detector; MHD sensor; Microbolometer; Microphone; Microwave chemistry sensor; Microwave radiometer; Mood sensor; Motion detector; Mouse; Multimeter; Net radiometer; Neutron detection; Nichols radiometer; Nitrogen oxide sensor; Nondispersive infrared sensor; Occupancy sensor; Odometer; Ohmmeter; Olfactometer; Optode; Oscillating U-tube; Oxygen sensor; Pain sensor; Particle detector; Passive infrared sensor; Pedometer; Pellistor; pH glass electrode; Photoplethysmograph; Photodetector; Photodiode; Photoelectric sensor; Photoionization detector; Photomultiplier; Photoresistor; Photoswitch; Phototransistor; Phototube; Piezoelectric accelerometer; Pirani gauge; Position sensor; Potentiometric sensor; Pressure gauge; Pressure sensor; Proximity sensor; Psychrometer; Pulse oximetry sensor; Pulse wave velocity monitor; Radio direction finder; Rain gauge; Rain sensor; Redox electrode; Reed switch; Resistance temperature detector; Resistance thermometer; Respiration sensor; Ring laser gyroscope; Rotary encoder; Rotary variable differential transformer; Scintillometer; Seismometer; Selsyn; Shack-Hartmann; Silicon bandgap temperature sensor; Smoke detector; Snow gauge; Soil moisture sensor; Speech monitor; Speed sensor; Stream gauge; Stud finder; Sudden Motion Sensor; Tachometer; Tactile sensor; Temperature gauge; Thermistor; Thermocouple; Thermometer; Tide gauge; Tilt sensor; Time pressure gauge; Touch switch; Triangulation sensor; Turn coordinator; Ultrasonic thickness gauge; Variometer; Vibrating structure gyroscope; Voltmeter; Water meter; Watt-hour meter; Wavefront sensor; Wired glove.; Yaw rate sensor; and Zinc oxide nanorod sensor. Although this disclosure describes particular types of sensors, this disclosure contemplates any suitable types of sensors.

A biosensor is a type of sensor that receives a biological stimulus and converts it into a data stream. As used herein, the term "biosensor" is used broadly. For example, a canary in a cage, as used by miners to warn of gas, could be considered a biosensor.

In particular embodiments, a biosensor is a device for the detection of an analyte. An analyte is a substance or chemical constituent that is determined in an analytical procedure. For instance, in an immunoassay, the analyte may be the ligand or the binder, while in blood glucose testing, the analyte is glucose. In medicine, analyte typically refers to the type of test being run on a patient, as the test is usually determining the presence or concentration of a chemical substance in the human body.

A common example of a commercial biosensor is the blood glucose biosensor, which uses the enzyme glucose oxidase to break blood glucose down. In doing so, it first oxidizes glucose and uses two electrons to reduce the FAD (flavin adenine dinucleotide, a component of the enzyme) to $FADH_2$ (1,5-dihydro-FAD). This in turn is oxidized by the electrode (accepting two electrons from the electrode) in a number of steps. The resulting current is a measure of the concentration of glucose. In this case, the electrode is the transducer and the enzyme is the biologically active component.

In particular embodiments, a biosensor combines a biological component with a physicochemical detector component. A typical biosensor comprises: a sensitive biological element (e.g., biological material (tissue, microorganisms, organelles, cell receptors, enzymes, antibodies, nucleic acids, etc.), biologically derived material, biomimic); a physicochemical transducer/detector element (e.g. optical, piezoelectric, electrochemical) that transforms the signal (i.e. input stimulus) resulting from the interaction of the analyte with the biological element into another signal (i.e. transducers) that may be measured and quantified; and associated electronics or signal processors generating and transmitting a data stream corresponding to the input stimulus. The encapsulation of the biological component in a biosensor may be done by means of a semi-permeable barrier (e.g., a dialysis membrane or hydrogel), a 3D polymer matrix (e.g., by physically or chemically constraining the sensing macromolecule), or by other means.

Some biosensor measurements are highly dependent the physical activity of the user prior to the measurement being made. For example, a user's fasting glucose level, serum-createnine level, and protein/createnine ratio may all vary based on the user's activity. Some users, in anticipation of a pending biosensor measurement, may increase their physical activity level in order to achieve a "better" analyte measurement. This may lead to misleading sensor measurements and possibly to false-negative disease state diagnoses. In particular embodiments, sensor network 100 may monitor and analyze a user's activity to ensure the user is not engaged in an abnormal level of physical activity before the biosensor measurement is made. In particular embodiments, sensor array 110 may include one or more accelerometers. These sensors may be worn, carried, or otherwise affixed to the user. The accelerometers may measure and transmit information regarding the user's activity level. Sensor array 110 may transmit data streams containing acceleration data of the user to analysis system 180. Analysis system 180 may analyze the accelerometer data to establish a baseline activity of the user, and also to monitor the user's activity prior to a biosensor measurement to ensure that the user's activity does not deviate from his baseline activity. Based on these deviations in activity, various alerts or warnings may be provided to the user or to the user's physician. Analysis system 180 may also analyze the accelerometer data to contextualize and normalize biosensor measurements. For example, accelerometer data that shows that a user was active during a certain time period may be used to explain an unusually low blood glucose measurement during the same period.

In particular embodiments, a sensor samples input stimulus at discrete times. The sampling rate, sample rate, or sampling frequency defines the number of samples per second (or per other unit) taken from a continuous stimulus to make a discrete data signal. For time-domain signals, the unit for sampling rate may be Hertz (1/s). The inverse of the sampling frequency is the sampling period or sampling interval, which is the time between samples. The sampling rate of a sensor may be controlled locally, remotely, or both.

In particular embodiments, one or more sensors in sensor array 110 may have a dynamic sampling rate. Dynamic sampling is performed when a decision to change the sampling rate is taken if the current outcome of a process is different from some specified value or range of values. For example, if the stimulus measured by a sensor is different from the outcome predicted by some model or falls outside some threshold range, the sensor may increase or decrease its sampling rate in response. Dynamic sampling may be used to optimize the operation of the sensors or influence the operation of actuators to change the environment.

In particular embodiments, a sensor with a dynamic sampling rate may take some predefined action when it senses the appropriate stimulus (light, heat, sound, motion, touch, etc.). For example, an accelerometer may have a default sample rate of 1/s, but may increase the sampling rate to 60/s whenever it measures a non-zero value, and then may return to a 1/s sampling rate after getting 60 consecutive samples equal to zero.

In particular embodiments, the dynamic sampling rate of a sensor may be based on input from one or more components of sensor network 100. As an example and not by way of limitation, a heart rate monitor may have a default sampling rate of 1/min. However, the heart rate monitor may increase its sampling rate if it senses that the user's activity level has increased, such as by a signal from an accelerometer. As another example and not by way of limitation, analysis system 180 may transmit instructions to one or more sensors instructing them to vary their sampling rates. As yet another example and not by way of limitation, the user's doctor may remotely activate or control a sensor.

In particular embodiments, a sensor with a dynamic sampling rate may increase or decrease the precision at which it samples input. As an example and not by way of limitation, a glucose monitor may use four bits to record a user's blood glucose level by default. However, if the user's blood glucose level begins varying quickly, the glucose monitor may increase its precision to eight-bit measurements.

In particular embodiments, the stimulus received by sensor 310 may be input from a person or user. A user may provide input in a variety of ways. User-input may include, for example, inputting a quantity or value into the sensor, speaking or providing other audio input to the sensor, and touching or providing other stimulus to the sensor. Any client system with a suitable I/O device may serve as a user-input sensor. Suitable I/O devices include alphanumeric keyboards, numeric keypads, touch pads, touch screens, input keys, buttons, switches, microphones, pointing devices, navigation buttons, stylus, scroll dial, another suitable I/O device, or a combination of two or more of these.

In particular embodiments, a sensor may query the user to input information into the sensor. In one embodiment, the sensor may query the user at static intervals (e.g., every hour). In another embodiment, the sensor may query the user at a dynamic rate. The dynamic rate may be based on a variety of factors, including prior input into the sensor, data from other sensors in sensor array 110, output from analysis system 180, etc. For example, if a heart-rate monitor in sensor array 110 indicates an increase in the user's heart-rate, the user-input sensor may immediately query the user to input his current activity.

In particular embodiments, an electronic calendar functions as a user-input sensor for gathering behavioral data. A user may input the time and day for various activities, including appointments, social interactions, phone calls, meetings, work, tasks, chores, etc. Each inputted activity may be further tagged with details, labels, and categories (e.g., "important," "personal," "birthday"). The electronic calendar may be any suitable personal information manager, such as Microsoft Outlook, Lotus Notes, Google Calendar, etc. The electronic calendar may then transmit the activity data as a data stream to analysis system 180, which could map the activity data over time and correlate it with data from other sensors in sensor array 110. For example, analysis system 180 may map a heart-rate data stream against the activity data stream from an electronic calendar, showing that the user's heart-rate peaked during a particularly stressful activity (e.g., dinner with the in-laws).

In particular embodiments, a data feed may be a sensor. A data feed may be a computing system that receives and aggregates physiological, psychological, behavioral, or environmental data from one or more sources and transmits one or more data streams based on the aggregated data. Alternatively, a data feed may be the one or more data streams based on the aggregated data. Example data feeds include stock-market tickers, weather reports, news feeds, traffic-condition updates, public-health notices, and any other suitable data feeds. A data feed may contain both personal and remote data, as discussed previously. A data feed may be any suitable computing device, such as computer system 1400. Although this disclosure describes particular types of data feeds, this disclosure contemplates any suitable types of data feeds.

Figure 4:
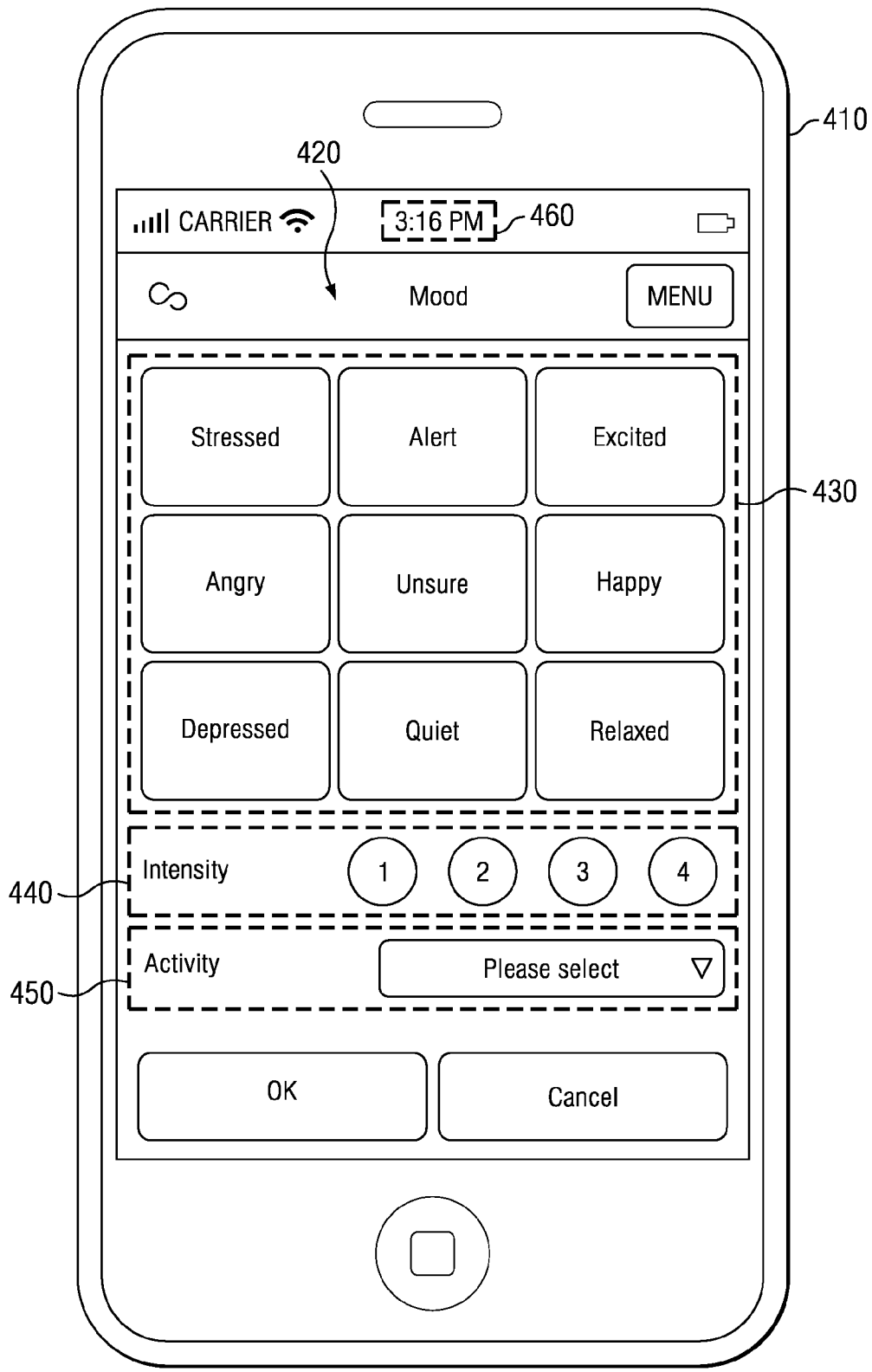
FIG. 4 illustrates an example sensor for collecting mood and activity information from a person.

FIG. 4 illustrates an example sensor for collecting mood and activity information from a person. This "mood sensor" 400 is a type of user-input sensor, that my receive input (i.e., stimulus) from a user regarding the user's psychological state and the user's behavior corresponding to that psychological state. Of course, it is possible for the user to record information about a 3rd party (e.g., a doctor recording information about a patient). However, this disclosure assumes that the user is recording information about himself, unless context suggests otherwise. Mood sensor 400 may be used to collect any type of user-input relating to psychological or behavioral aspects of the person. The example embodiments illustrated in FIG. 4 and described herein are provided for illustration purposes only and are not meant to be limiting.

In particular embodiments, mood sensor 400 includes a software application that may be executed on client system 410. FIG. 4 illustrates a smart phone as an example client system 410, however any suitable user-input device may be used (e.g., cellular phone, personal digital assistant, personal computer, etc.). In particular embodiments, a user may execute an application on client system 410 to access mood collection interface 420. In other embodiments, a user may use a browser client or other application on client system 410 to access mood collection interface 420 over a mobile network (or other suitable network). Mood collection interface 420 is configured to receive signals from the user. For example, the user may click, touch, or otherwise interact with mood collection interface 420 to select and input mood and behavior information, and to perform other actions.

Mood collection interface 420 may include various components. FIG. 4 illustrates mood input widget 430, mood intensity input widget 440, activity input widget 450, and clock 460, however other components are possible. Mood input widget 430 is a three-by-three grid of mood icons, wherein each icon has a unique semantic label and color. The grid illustrated in FIG. 3 shows the following example moods and colors:

| Mood | Color |
|---|---|
| Stressed | Yellow |
| Alert | Orange |
| Excited | Pink |
| Angry | Red |
| Unsure | Grey |
| Happy | Green |
| Depressed | Maya blue |
| Quiet | Mauve |
| Relaxed | Light cornflower blue |

The user may touch one or more of the mood icons to input his current mood. Mood intensity widget 440 is a row with numbered icons ranging from one to four that each correspond to a level of intensity of a mood. The numbers range from the lowest to highest intensity, with one being the lowest and four being the highest. The user may touch one of the numbers to input an intensity corresponding to a selected mood. In particular embodiments, the mood intensity corresponds to a standard psychometric scale (e.g., Likert scale). Activity input widget 450 is a drop-down menu containing a list of activities. The list is not illustrated, but could include a variety of activities, such as sleeping, eating, working, driving, arguing, etc. The user may touch the drop-down menu to input one or more activities corresponding to a selected mood. Clock 460 provides the current time according to client system 410. This time may be automatically inputted as a timestamp to any other inputs on mood collection interface 420. In particular embodiments, a time or duration of the mood may be inputted manually by the user. The input widgets described above are provided as examples of one means for gathering mood, intensity, and activity data, and are not meant to be limiting. A variety of other input means could be utilized. In particular embodiments, the mood, mood intensity, activity, and time may all be entered manually by the user, without the use of widgets, icons, drop-down menus, or timestamps. This would allow the user to input a variety of mood, intensity, and activity information for any time or time period.

In particular embodiments, mood sensor 400 is a sensor in sensor array 110. After receiving the mood, intensity, activity, and time inputs, the mood sensor 400 may transmit the data as one or more data streams to analysis system 180.

In particular embodiments, mood sensor 400 may query the user to input his mood, activity, and possibly other information. In one embodiment, mood sensor 400 queries the user at fixed time intervals (e.g., every hour). In another embodiment, mood sensor 400 queries the user at a dynamic rate. The dynamic rate may be based on a variety of factors, including the user's prior mood and activity inputs, data from other sensors in sensor array 110, output from analysis system 180, etc. For example, if the user inputs that he is "angry" with an intensity of "4," mood sensor 400 may begin querying the user every 15 minutes until the user indicates the intensity of his mood has dropped to "2" or less. In another example, if a heart-rate monitor in sensor array 110 indicates an increase in the user's heart-rate, mood sensor 400 may query the user to input his current mood and activity. In yet another example, if the user's electronic calendar indicates that he has an appointment tagged as "important," mood sensor 400 may query the user to input his mood immediately before and after the appointment.

In particular embodiments, mood sensor 400 may administer one or more therapies or therapeutic feedbacks. A therapy may be provided based on a variety of factors. In one embodiment, mood sensor 400 may provide therapeutic feedback to the user either during or after the user inputs a negative mood or activity. For example, if the user touches the "angry" button, the display may change to show a calming image of puppies playing in the grass. In another embodiment, mood sensor 400 may provide therapeutic feedback to the user based on output from analysis system 180. For example, if a heart-rate monitor in sensor array 110 indicates an increase in the user's heart-rate, and the user inputs "stressed" into mood sensor 400, the analysis system 180 may determine that a therapeutic feedback is needed. In response to this determination, mood sensor 400 may play relaxing music to clam the user. Mood sensor 400 may deliver a variety of therapies, such as interventions, biofeedback, breathing exercises, progressive muscle relaxation exercises, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, and other therapeutic feedbacks. Mood sensor 400 may also provide information on where the user can seek other therapies, such as specific recommendations for medical care providers, hospitals, etc.

In particular embodiments, mood sensor 400 may be used to access and display data related to the user's psychology and behavior on display system 190. Display system 190 may display data on mood collection interface 420 (i.e., the smartphone's touch screen) or another suitable display. Mood sensor 400 may access a local data store (e.g., prior mood and activity input stored on the user's smart phone) or a remote data store (e.g., medical records from the user's hospital) over any suitable network. In one embodiment, mood sensor 400 may access and display mood and activity information previously recorded by mood sensor 400. For example, the user could click on the "happy" button to access data showing the mood intensity, activity, and time associated with each input of "happy" by the user on mood sensor 400. In another embodiment, mood sensor 800 may access and display data recorded by other medical sensors or medical procedures. For example, the user could click on the "depressed" button to access data from one or more other sensors in sensor array 110 (e.g., heart-rate sensor data, pulse oximetry sensor data, etc.) that correspond to each input of "depressed" by the user on mood sensor 400.

Figure 5:
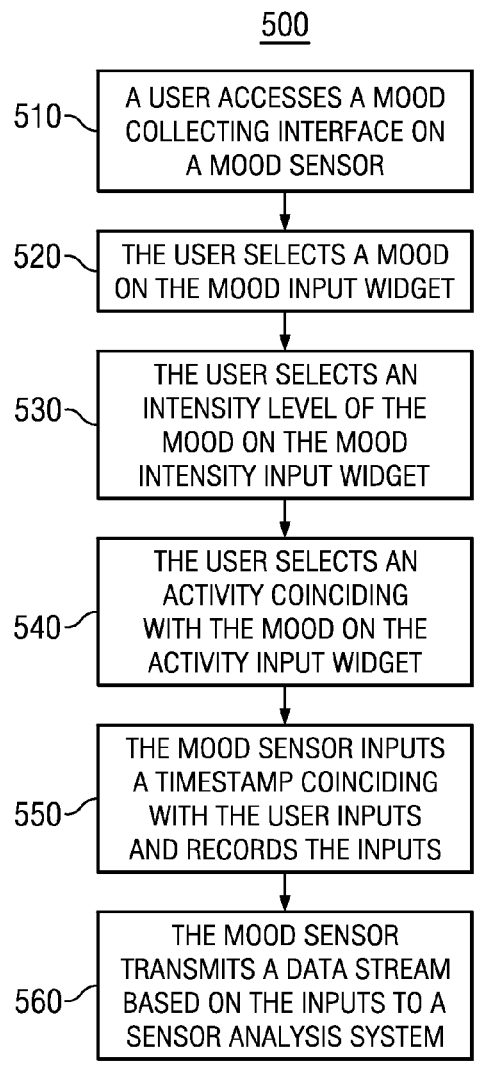
FIG. 5 illustrates an example method for collecting mood and activity information from a person.

FIG. 5 illustrates an example method 500 for collecting mood information from a person. A user of mood sensor 400 may first access mood collection interface 420 on client system 410 at step 510. The user may select one or more moods on mood input widget 430 by touching one of the mood icons at step 520. The user may select an intensity level of the selected mood on mood intensity input widget 440 at step 530. The user may select an activity coinciding with the selected mood on activity input widget 450 at step 540. After all three inputs are entered by the user, mood sensor 400 may automatically record the inputs or the user may indicate that he is done inputting moods and activities by clicking "ok" or providing some other input at step 550. At this step, the mood sensor may also record a time indication coinciding with the inputs. Finally, mood sensor 400 may transmit a data stream based on one or more of the mood, intensity, activity, or time inputs to analysis system 180 at step 560. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components carrying out particular steps of the method of FIG. 5, this disclosure contemplates any suitable combination of any suitable components carrying out any suitable steps of the method of FIG. 5.

Figure 6:
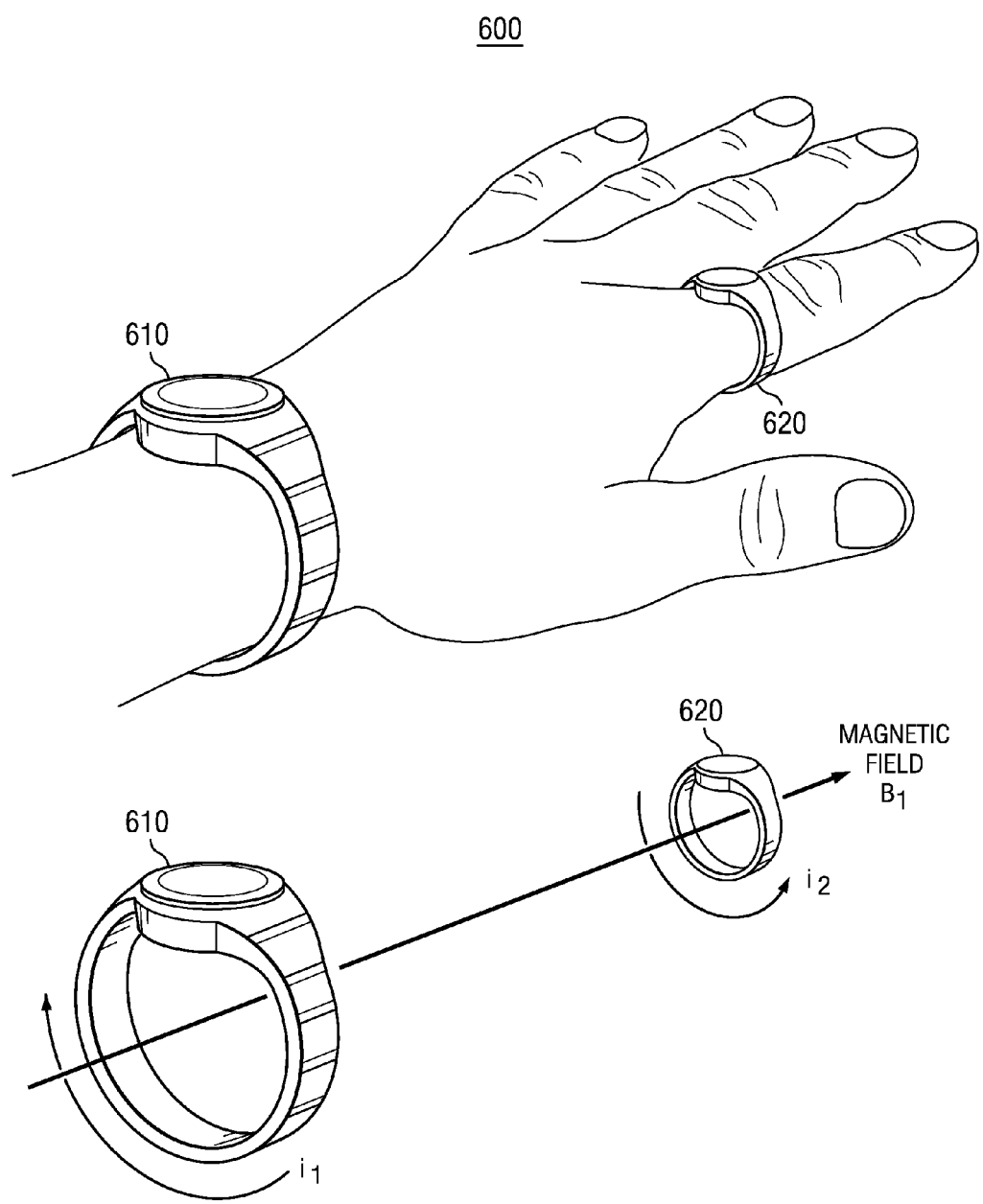
FIG. 6 illustrates an example inductively-powered ring-based sensor.

FIG. 6 illustrates an example of an inductively-powered ring-based sensor. In particular embodiments, ring-based sensor 600 comprises a wrist element 610 and a ring element 620. In particular embodiments, ring element 620 is a ring that may be worn or affixed on a user's finger and contains a sensing element. In one embodiment, ring element 620 is an implanted (subcutaneous) device. In particular embodiments, wrist element 610 may be a band, bracelet, or cuff. In one embodiment, wrist element 610 is a wrist watch.

In particular embodiments, ring element 620 may include one or more types of sensors. For example, ring element 620 may include a pulse oximeter, heart-rate monitor, a CO-oximeter, a galvanic-skin-response sensor, an electrocargiograph, a respirometer, another suitable sensor, or two or more such sensors.

In particular embodiments, ring-based sensor 600 is a pulse oximeter. A pulse oximeter is type of sensor that indirectly measures the oxygen saturation ($SpO_2$) of a user's blood. Pulse oximeters typically measure the percentage of arterial hemoglobin in the oxyhemoglobin configuration (i.e., saturated hemoglobin). Typical $SpO_2$ percentages range from 95-100%, however lower percentages are not uncommon. An estimate of arterial $pO_2$ may be made from the pulse oximeter's $SpO_2$ measurements. In particular embodiments, ring-based sensor 600 utilizes two different light sources, usually red and infrared, that measure different absorption or reflection characteristics for oxyhemoglobin (bright red) and deoxyhemoglobin (dark-red/blue). Based upon the ratio of changing absorbances of the red and infrared light caused by the difference in color between oxygen-bound (bright red) and unbound (dark-red/blue) hemoglobin in the blood, a measure of oxygenation (i.e., the percent of hemoglobin molecules bound with oxygen molecules) may be made. In particular embodiments, ring-based sensor 600 determines blood oxygen saturation by transmission oximetry. Transmission oximetry operates by transmitting light through an appendage, such as a finger or an earlobe, and comparing the characteristics of the light transmitted into one side of the appendage with that detected on the opposite side. In other embodiments, ring-based sensor 600 determines blood oxygen saturation by reflectance oximetry, which uses reflected light to measure blood oxygen saturation. In a typical pulse oximeter, the monitored signal varies in time with the heartbeat of the user because the arterial blood vessels expand and contract with each heartbeat. In particular embodiments, ring-based sensor 600 may normalize the monitored signal (e.g., by subtracting minimum absorption from peak absorption), allowing it to measure absorption caused by arterial blood. In particular embodiments, ring element 620 comprises two light-emitting diodes (LEDs), which face a photodiode on the opposite side of the ring. When worn, the LEDs can emit light through a user's translucent finger. One LED may be red, with a wavelength of, for example, 660 nm, and the other may be infrared, with a wavelength of, for example, 905, 910, or 940 nm. Absorption at these wavelengths differs significantly between oxyhemoglobin and its deoxygenated form; therefore, the oxy/deoxyhemoglobin ratio may be calculated from the ratio of the absorption of the red and infrared light.

In particular embodiments, ring element 620 may be powered by electromagnetic induction. Wrist element 610 comprises an inductive power source. Wrist element 610 may generate a first current ($i_1$) through one or more loops in the wrist element. The current in wrist element 610 may generate a magnetic field ($B_1$). If the magnetic flux passing through ring element 620 is varied over time, it may inductively generate a second current ($i_2$) through one or more loops in ring element 620. A time-varying magnetic flux through ring element 620 may be created using a variety of means. In one embodiment, current $i_1$ is an alternating current, which generates a magnetic field $B_1$ that varies in time with the alternating current. The amount of magnetic flux passing through ring element 620 may vary as magnetic field $B_1$ varies. In another embodiment, current $i_1$ is a direct current, which generates a static magnetic field $B_1$. The amount of magnetic flux passing through ring element 620 may vary as the user moves his finger through the static magnetic field $B_1$ generated by wrist element 610, such that the natural movement of the user's finger is sufficient to power ring element 620.

In particular embodiments, ring element 620 includes a wireless transmitter and wrist element 610 includes a wireless transceiver. These allow ring element 620 to communicate with wrist element 610 using a variety of communication means. In particular embodiments, ring element 620 and wrist element 610 may communicate using RF induction technology. In other embodiments, ring element 620 and wrist element 610 may communicate using other communication means (e.g., radio, Bluetooth, etc.). Ring element 620 may transmit absorption measurements to wrist element 610 for further processing, analysis, and display.

In particular embodiments, ring-based sensor 600 is a sensor in sensor array 110. Ring-based sensor 600 may transmit sensor data as one or more data streams to analysis system 180. In particular embodiments, wrist element 610 may include a local analysis system 120. In other embodiments, wrist element 610 may transmit sensor data as one or more data streams to remote analysis system 150. Analysis system 180 may transmit one or more analysis outputs to display system 190. In particular embodiments, wrist element 610 includes a local display system 130 that shows current measurements by the ring-based sensor 600. In other embodiments, measurements by the ring-based sensor 600 are displayed on remote display system 140.

Figure 7:
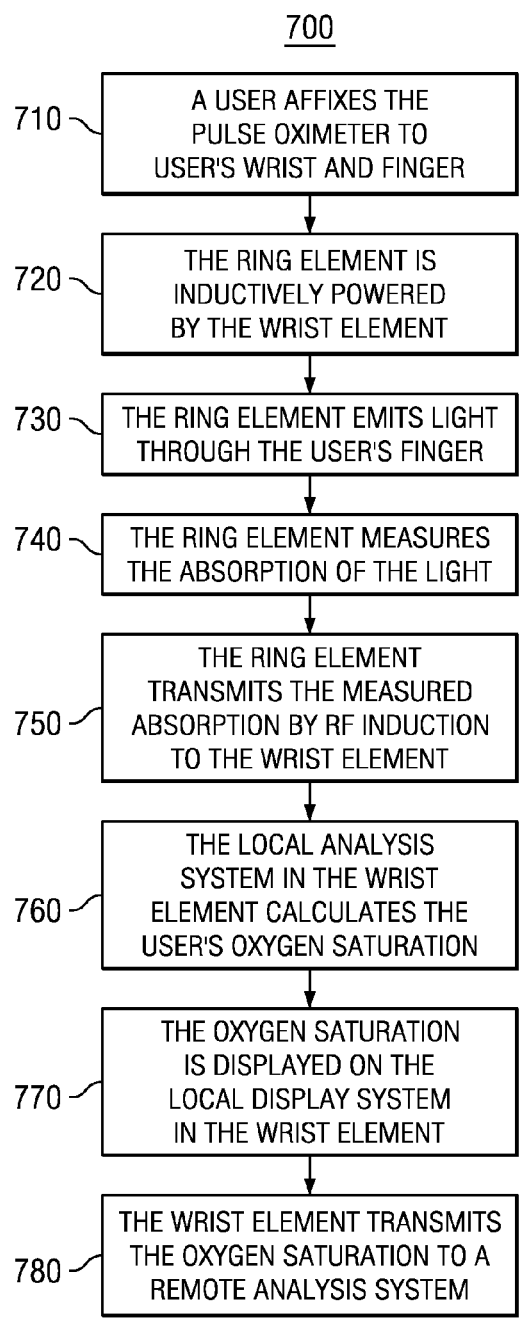
FIG. 7 illustrates an example method using an inductively-powered ring-based sensor.

FIG. 7 illustrates an example method using an inductively-powered ring-based sensor, wherein wrist element 610 contains a pulse oximeter. A user of ring-based sensor 600 may first affix wrist element 610 and ring element 620 on his wrist and finger, respectively, at step 710. Once affixed, wrist element 610 may inductively power ring element 620 at step 720. Ring element 620 may then emit light of two or more wavelengths through the user's finger at step 730. Ring element 620 may then measure the absorption of the light at step 740. Ring element 620 may then transmit the measured absorption to wrist element 610 using RF induction technology at step 750. Local analysis system 120 in wrist element 610 may then calculate the user's current oxygen saturation based on the measured absorption at step 760. Local display system 130 in wrist element 610 may also display the user's current oxygen saturation at step 770. Finally, wrist element 610 may transmit a data stream based on oxygen saturation calculation to remote analysis system 150 at step 780. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components carrying out particular steps of the method of FIG. 7, this disclosure contemplates any suitable combination of any suitable components carrying out any suitable steps of the method of FIG. 7.

Figure 8:
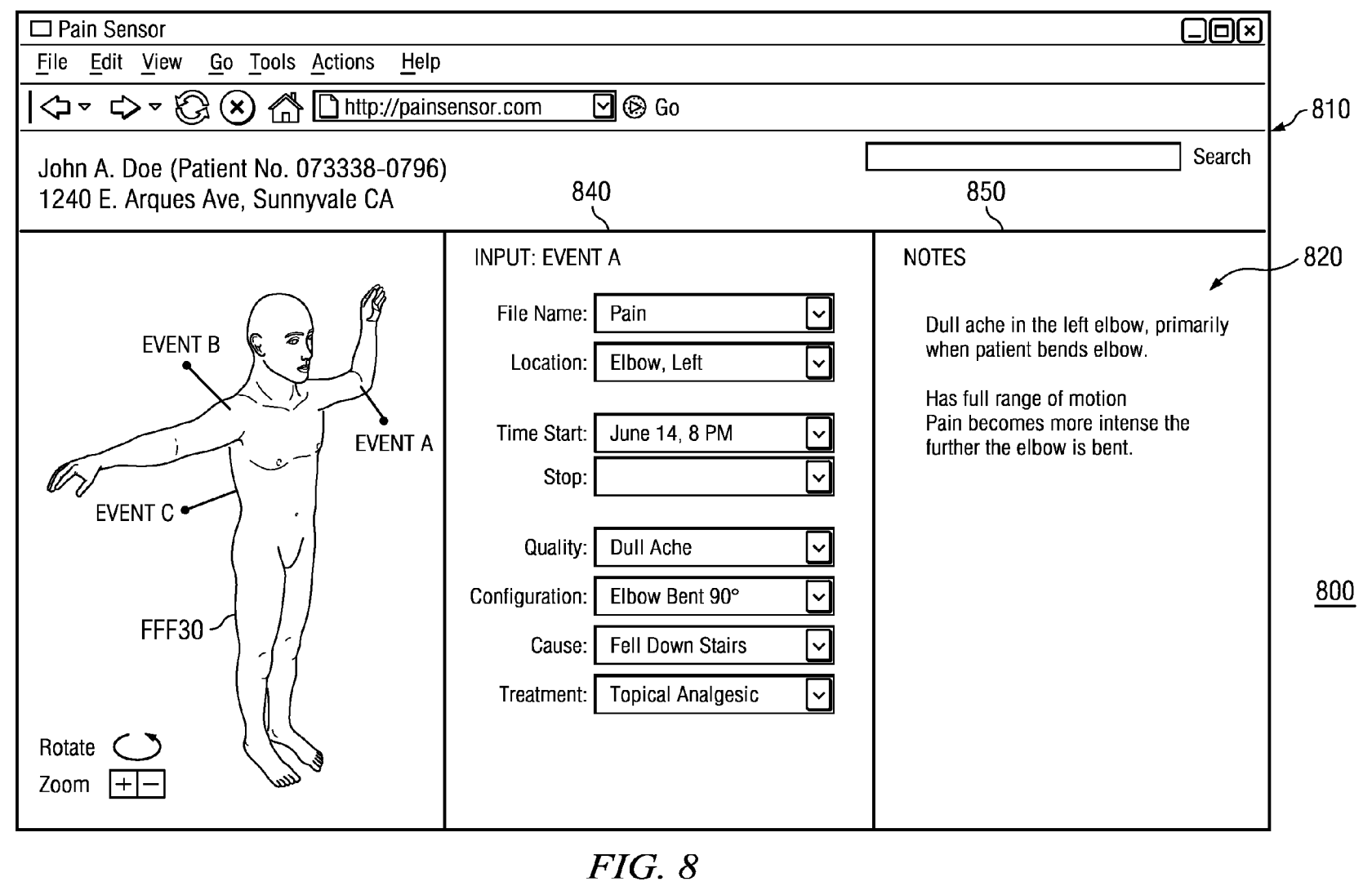

FIG. 8 illustrates an example sensor for collecting information of a physiological event on a three-dimensional representation of a person's body. Physiological event sensor 800 ("pain sensor") is a type of user-input sensor, which receives input (i.e., stimulus) from a user regarding a physiological event on or in the user's body. Of course, it is possible for the user to record information about a 3rd party (e.g., a doctor recording information about a patient). However, this disclosure assumes that the user is recording information about himself, unless otherwise specified. Pain sensor 800 may be used to collect any type of physiological information related to a person, including pain. The example embodiments illustrated in FIG. 8 and described herein are provided for illustration purposes only and are not meant to be limiting.

In particular embodiments, pain sensor 800 includes a software application that may be executed on any suitable client system. FIG. 8 illustrates a webpage-based application accessed from browser client 810, however any user-input application on any suitable user-input device may be used. In particular embodiments, a user may use browser client 810 to access pain sensor interface 820 over the internet (or other suitable network). Pain sensor interface 820 may be automatically generated and presented to the user in response to the user visiting or accessing a website or executing an application on a suitable client system with a suitable browser client.

A networking system may transmit data to the client system, allowing it to display the pain sensor interface 820, which is typically some type of graphic user interface. For example, the webpage downloaded to the client system may include an embedded call that causes the client system to download an executable object, such as a Flash .SWF object, which executes on the client system and renders one or more components of the interface within the context of the webpage. Other interface types are possible, such as server-side rendering and the like. Pain sensor interface 820 is configured to receive signals from the user via the client system. For example, the user may click on pain sensor interface 820, or enter commands from a keyboard or other suitable input device.

The pain sensor interface 820 may include various components. FIG. 8 illustrates a three-dimensional graphical model of the user ("3D avatar") 830 and an interface for inputting and displaying physiological event information 840. In particular embodiments, a user may input one or more details regarding a certain physiological event on pain sensor interface 820. In one embodiment, a user may input the location of a physiological event on or in the user's body by clicking on the appropriate location of the 3D avatar 830 (e.g., clicking on the avatar's left elbow). The user may also be able to select a depth, area, or volume associated with the physiological event. The user may then use interface 840 to input further details regarding the physiological event, such as the type of physiological event (e.g., pain, itching, wound, etc.), a time range associated with the physiological event (e.g., when the pain started and stopped, when the wound was inflicted, etc.), a quality or intensity associated with the physiological event (e.g., a dull ache, mild itching, etc.), and a cause of the physiological event (e.g., skiing accident, contact with poison oak, etc.). One of ordinary skill in the art would recognize that the types of details associated with a physiological event described above are not comprehensive, and that a variety of other details related to a physiological event may be inputted into pain sensor 800.

In particular embodiments, the user may input one or more treatments used for the physiological event (e.g., acupuncture, ice, bandage, oral analgesic, etc.). In particular embodiments, details regarding the treatment (e.g., time/duration/frequency, location, dose, quality, care provider, etc.) may also be inputted.

In particular embodiments, the user may input one or more configurations of the body associated with the physiological event. In particular embodiments, the user may do this by manipulating the 3D avatar 830 to illustrate the configuration of the body associated with the physiological event. For example, the user could click on the 3D avatar's left elbow to cause it to bend to a certain position associated with a pain. The user may also be able to rotate the 3D avatar 830 around one or more axes.

In particular embodiments, the display of 3D avatar 830 may alter in response to the input provide by the user. For example, the avatar may alter to show certain treatments (e.g., displaying a cast on the avatar's leg if a cast has been applied to the user). In another example, the avatar may alter to reflect the physiological event (e.g., inputting information on pain in the left elbow may cause the left elbow on the 3D avatar to glow red in the display). In yet another example, the avatar may be customizable to reflect the particular anatomy of the person represented (e.g., displaying appropriate genitals for female versus male user, altering the dimensions of the avatar to reflect the height and weight of the user, etc.). 3D avatar 830 may be customized and altered in a variety of ways, and the examples above are not meant to be limiting.

In particular embodiments, pain sensor 800 is a sensor in a sensor array 110. After receiving input on the details of the physiological event, pain sensor 800 may transmit the data as a data stream to analysis system 180.

In particular embodiments, pain sensor 800 may be used to access and display data related to the user's body on display system 190. Display system 190 may display data on pain sensor interface 820 or another suitable display. Pain sensor 800 may access a local data store (e.g., prior pain sensor input stored on the user's personal computer) or a remote data store (e.g., medical records from the user's hospital) over any suitable network. In one embodiment, pain sensor 800 may access and display physiological event information previously recorded by the pain sensor. For example, the user could click on the right shoulder of 3D avatar 830 to access data on one or more past physiological events on the person's right shoulder that were recorded by pain sensor 800. In another embodiment, pain sensor 800 may access and display data recorded by other medical sensors or medical procedures. For example, the user could click on the spine of 3D avatar 830, and pain sensor 800 could access medical records from other sensors or procedures related to the person's spine (e.g., MRI results, CAT scans, surgical records, etc.).

In one embodiment, pain sensor 800 may conform to the Systematized Nomenclature of Medicine ("SNOMED") standard. Pain sensor 800 may be able to receive user-input in SNOMED format (e.g., the user could input 22298006 to record a myocardial infarction) or to transmit a data stream with data in SNOMED format (e.g., if the user inputs a burn on his skin, the pain sensor could transmit a data stream containing the code 284196006). Various embodiments may conform with one or more other medical terminology standards, and this example is not meant to be limiting.

Figure 9:
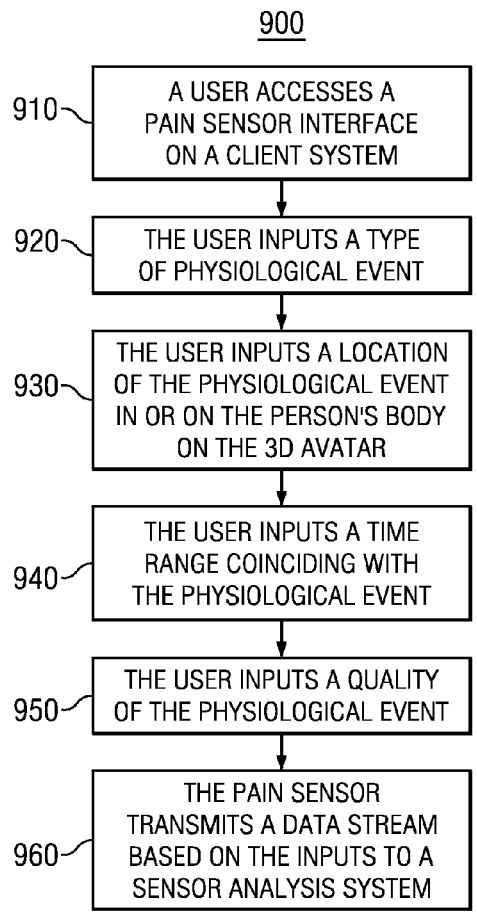
FIG. 9 illustrates an example method for collecting information of a physiological event on a three-dimensional representation of a person's body.

FIG. 9 illustrates an example method 900 for collecting physiological event information from a person. A user of pain sensor 800 may first access pain sensor interface 420 from browser client 810 at step 910. The user may input one or more types of physiological events on interface 840 at step 920. The user may input a location of the physiological event in or on the person's body on 3D avatar 830 at step 930. The user may input a time range coinciding with the inputted physiological event at step 940. The user may input a quality of the physiological event at step 950. After this step, pain sensor 800 may automatically record the inputs, or may wait for the user to indicate that he is done inputting information by clicking "record event" or providing some other input. Finally, pain sensor 800 may transmit a data stream based on one or more of the inputs to analysis system 180 at step 960. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates particular components carrying out particular steps of the method of FIG. 9, this disclosure contemplates any suitable combination of any suitable components carrying out any suitable steps of the method of FIG. 9.

A data stream comprises one or more datum transmitted from a sensor. A data stream is a digital or analog signal that may be transmitted over any suitable transmission medium and further used in electronic devices. Sensor array 110 may transmit one or more data streams based on one or more stimuli to one or more analysis systems 180 over any suitable network.

A data stream may include signals from a variety of types of sensors, including physiological, psychological, behavioral, and environmental sensors. A sensor generates a data stream corresponding to the stimulus is receives. For example, a physiological sensor (e.g., an accelerometer) generates a physiological data stream (e.g., an accelerometer data stream, which includes, for example, data on the acceleration of a person over time).

In particular embodiments, a sensor transmits one or more datum at discrete times. The transmitting rate, transmission rate, or transmitting frequency defines the number of transmissions per second (or per other unit) sent by a sensor to make a discrete data signal. For time-domain signals, the unit for transmitting rate may be Hertz (1/s). The inverse of the transmitting frequency is the transmitting period or transmitting interval, which is the time between transmissions. The datum may be transmitted continuously, periodically, randomly, or with any other suitable frequency or period. This may or may not correlate with the sampling rate of the sensor.

In particular embodiments, the components of sensor network 100 may utilize some type of data acquisition system to further process the data stream signal for use by analysis system 180. For example, a data acquisition system may convert an analog waveforms signal into a digital value. The data acquisition system may be local, for example, integrated into a sensor in sensor array 110 or into local analysis system 120. The data acquisition system may also be remote, for example, integrated into remote analysis system 150 or an independent system.

In particular embodiments, the data acquisition system may perform one or more signal conditioning processes, for example, if the signal from the sensor is not suitable for the type of analysis system being used. For example, the data acquisition system may amplify, filter, or demodulate the signal. Various other examples of signal conditioning might be bridge completion, providing current or voltage excitation to the sensor, isolation, and linearization. In particular embodiments, single-ended analog signals may be converted to differential signals. In particular embodiments, digital signals may be encoded to reduce and correct transmission errors or down-sampled to reduce transmission power requirements.

In particular embodiments, the components of sensor network 100 may utilize some type of data logging system to record, categorize, and file data from one or more data streams over time. The data logging system may be local, for example, integrated into a sensor in sensor array 110 or into local analysis system 120. The data logging system may also be remote, for example, integrated into remote analysis system 150 or an independent system. The data logging system may also use distributed resources to record data.

The data logging system may record data streams as one or more data sets. A data set comprises one or more datum from a data stream. Data sets may be categorized and formed based on a variety of criteria. For example, a data stream could be recorded as one or more data sets based on the specific user, sensor, time period, event, or other criteria.

Analysis system 180 may monitor, store, and analyze one or more data streams from sensor array 110. A data stream from sensor array 110 may be transmitted to analysis system 180 over any suitable medium. Analysis system 180 may transmit one or more analysis outputs based on the one or more data streams to one or more display systems 190. Analysis system 180 may be any suitable computing device, such as computer system 1400.

Analysis system 180 comprises one or more local analysis systems 120 and/or one or more remote analysis systems 150. Where analysis system 180 comprises multiple subsystems (e.g., local analysis system 120 and remote analysis system 150), processing and analysis of the data streams may occur in series or in parallel. In one embodiment, analysis system 180 receives identical data streams from a sensor at both local analysis system 120 and remote analysis system 150. In another embodiment, analysis system 180 receives a data stream at local analysis system 120, which performs some local analysis and then transmits a modified data stream/analysis output to remote analysis system 150.

Analysis system 180 may analyze a data stream in real-time as it is received from sensor array 110. Analysis system 180 may also selectively access and analyze one or more data sets from a data stream. In particular embodiments, analysis system 180 may perform a variety of processes and calculations, including ranging, inspecting, cleaning, filtering, transforming, modeling, normalizing, averaging, correlating, and contextualizing data. Analysis system 180 may use a variety of data analysis techniques, including data mining, data fusion, distributed database processing, and artificial intelligence. These techniques may be applied to analyze various data streams and to generate correlations and conclusions based on the data. Although this disclosure describes performing particular analytical processes using particular analysis techniques, this disclosure contemplates performing any suitable analytical processes using any suitable analysis techniques.

In particular embodiments, analysis system 180 may generate models based on one or more data streams. A model is a means for describing a system or object. For example, a model may be a data set, function, algorithm, differential equation, chart, table, decision tree, binary decision diagram, simulation, another suitable model, or two or more such models. A model may describe a variety of systems or objects, including one or more aspects of a person's physiology, psychology, behavior, or environment.

Analysis system 180 may generate models that are empirical, theoretical, linear, nonlinear, deterministic, probabilistic, static, dynamic, heterogeneous, or homogenous. Analysis system 180 may generate models that fit one or more data points using a variety of techniques, including, for example, curve fitting, model training, interpolation, extrapolation, statistical modeling, nonparametric statistics, differential equations, etc.

Analysis system 180 may generate models of various types, including baseline models, statistical models, predictive models, etc. A baseline model is a model that serves as a basis for comparison, and is typically generated using controlled data over a specified period. A predictive model is a mathematical function (or set of functions) that describe the behavior of a system or object in terms of one or more independent variables. For example, a predictive model that may be used to calculate a physiological state based on one or more actual sensor measurements. A type of predictive model is a statistical model, which is a mathematical function (or set of functions) that describe the behavior of an object of study in terms of random variables and their associated probability distributions. One of the most basic statistical models is the simple linear regression model, which assumes a linear relationship between two measured variables. In particular embodiments, a predictive model may be used as a baseline model, wherein the predictive model was generated using controlled data over a specified period.

In one embodiment, analysis system 180 may generate a model by normalizing or averaging data from one or more data streams. For example, a model of a data stream from a single sensor could simply be the average sensor measurement made by the sensor over some initialization period. In another example, a model could be a single sensor measurement made during a control period.

In another embodiment, analysis system 180 may generate a model by fitting one or more data sets to a mathematical function. For example, a model could be an algorithm based on sensor measurements made by one or more sensors over some control period. The model may include a variety of variables, including data from one or more data streams and one or more fixed variables. The following is an example algorithm that analysis system 180 could generate to model a system or object:

$$f_m = f(D_{sensor}^1, \ldots, D_{sensor}^N, X^1, \ldots, X^M)$$

where:
$f_m$ is the model,
$(D_{sensor}^1, \ldots, D_{sensor}^N)$ are data streams 1 through N, and
$(X^1, \ldots, X^N)$ are fixed variables 1 through M.

In particular embodiments, the model may be used to predict hypothetical sensor measurements in theoretical or experimental systems. In other embodiments, the model may be used to determine or categorize a user's physiological or psychological state. For example, the model may determine a user's risk for a certain disease state with an abstract or statistical result. The model could simply identify the user as being at "high risk" of developing a disease, or identify the user as being 80% likely to develop the disease. In another example, the model may determine a user's severity or grade of a disease state.

In particular embodiments, analysis system 180 may map one or more data streams over time, allowing the data streams to be compared.

Mapping and comparing the data streams allows analysis system 180 to contextualize and correlate a data set from one data stream with data sets from one or more other data streams. In particular embodiments, analysis system 180 contextualizes and correlates data sets from the data streams where the data stream exhibits some type of deviation, variability, or change.

Contextualizing is the process of interpreting a data set against the background of information provided by one or more data streams. Correlating is establishing or demonstrating a causal, complementary, parallel, or reciprocal relation between one data set and another data set. In general, analysis system 180 may make more accurate correlations as more data becomes available from sensor array 110.

In particular embodiments, analysis system 180 may contextualize and correlate a data set from a data stream that exhibits some type of deviation, variability, or change from other data sets in the data stream. For example, a user may be wearing a heart-rate monitor and an accelerometer, which transmit a heart-rate data stream and an accelerometer data stream, respectively. A data set in the heart-rate data stream may show the user had an elevated heart-rate during a certain time period. A data set in the accelerometer data stream may show the user had an elevated activity during the same time period. By mapping and comparing these data sets, analysis system 180 may contextualize and correlate the data streams. For example, an elevated heart-rate that coincides with increased activity is typically a normal response. However, a spike in heart-rate that coincides with a marginal elevated physical activity may not be a normal response. Analysis system 180 could then determine, based on the comparison, whether certain levels of activity produce abnormal heart-rate spikes in the user.

In particular embodiments, sensor array 110 comprises a heart-rate sensor, a mood sensor 400 (for collecting subjective stress and behavior information) that is a smart phone, and a GPS system that is built into the smart phone. This system may be used to contextualize and correlate physiological, psychological, behavioral and environmental data steams to diagnose and monitor stress in a user. For example, the heart-rate sensor's data stream may show a spike in the user's heart-rate at certain times of the day or at certain location. Similarly, mood sensor 400's data stream, when mapped against the heart-rate data, may show these periods of increased heart-rate correlate to periods when the user indicated that his mood was "stressed" and his activity was "driving." If the user has previously been diagnoses as hypertensive, it may be desirable to avoid these particularly stressful driving situations that cause a spike in the user's heart-rate. These stressful driving situations may be identified by contextualizing the prior data streams against the GPS system's data stream. When the location data from the GPS system is mapped against the prior data streams, it may show the heart-rate spikes, stressed mood, and driving, all occurred at a specific highway interchange. Therefore, by contextualizing the physiological, psychological, behavioral, and environmental data streams, analysis system 180 may identify driving on the specific highway interchange as the cause of the user's heart-rate spikes. This could be useful, for example, to allow the user to identify situations to avoid (e.g., the specific highway interchange) and possibly to identify better or healthier alternatives (e.g., taking surface streets).

Sensor array 110 may continuously transmit data regarding a user's health to analysis system 180, which may monitor and automatically detect changes in the user's health state. As used herein, "health state" refers to a person's physiological and psychological state, including the person's state with respect to pathologies and diseases. By using an integrated sensor array 110 to monitor physiological, psychological, behavioral, and environmental factors, analysis system 180 may identify pathologies, disease states, and other health-related states with greater accuracy than is possible with any individual sensor.

In particular embodiments, one or more sensors in sensor array 110 may measure one or more biomarkers. A biomarker is a characteristic that may be measured and evaluated as an indicator of biological processes, pathogenic processes, or pharmacologic responses. For example, in a pharmacogenomic context, a biomarker would be a specific genetic variation that correlates with drug response. In another example, in a neurochemical context, a biomarker would be a person's subjective stress level that correlates with the person's plasma glucocorticoid level. A biomarker is effectively a surrogate for measuring another physiological or psychological characteristic. A biomarker may include any type of stimulus, including physiological, psychological, behavioral, and environmental stimulus.

In particular embodiments, analysis system 180 may identify pathologies, disease states, and other health states of a user. For example, analysis system 180 could determine whether a user has hypertension by monitoring a blood pressure data stream for a three week period and identifying substantial periods where the user's blood pressure is at least 140/90 mmHg. The accuracy of identification may generally be increased as the number of data streams is increased. Analysis system 180 may contextualize and correlate data from multiple data streams to eliminate confounders from its data analysis and reduce the likelihood of generating false-positive and false-negative disease-state diagnoses. For example, the hypertension diagnosis system described above may generate a false-positive diagnosis of hypertension if the user engages in lengthy periods of physical activity, which naturally raise the user's blood pressure. In this example, if analysis system 180 also monitored a heart-rate data stream of the user, it could eliminate blood pressure data sets that correlate with time periods of high heart-rate, thereby reducing the likelihood of generating an incorrect hypertension diagnosis.

In particular embodiments, analysis system 180 may analyze physiological, psychological, behavioral and environmental data steams to identify correlations between certain data sets. These correlations may be of varying degrees of dependence (e.g, as determined by a Pearson's product-moment coefficient). Analysis system 180 may then use these correlations to generate causality hypotheses of varying degrees of confidence. For example, analysis system 180 may be able to correlate a behavioral data set indicating the user had a fight with a physiological data set indicating the user had an elevated heart-rate to identify the fight as the cause of the elevated heart-rate. In another example, analysis system 180 may be able to correlate a physiological data set indicating the user had an elevated skin temperature with a behavioral data set indicating the user was engaged in physical activity to identify the physical activity as the cause of the elevated skin temperature. In yet another example, analysis system 180 may be able to correlate a psychological data set indicating the user is depressed with an environmental data set indicating that the user's stock portfolio declined to identify the stock decline as the cause of the user's depression. Analysis system 180 may use a variety of methods to identify correlations and generate causality hypotheses.

In particular embodiments, analysis system 180 may generate a model of a user's health state. In one embodiment, analysis system 180 may generate a baseline model of the user's physiological or psychological state by analyzing one or more data streams during a control period. Once the baseline model is established, analysis system 180 could then continuously monitor the user and identify deviations, variability, or changes in the data streams as compared to the baseline model. In another embodiment, analysis system 180 may generate a predictive model of the user's physiological or psychological state by analyzing one or more data streams and generating one or more algorithms that fit the sensor measurements. Once the predictive model is established, analysis system 180 could then be used to predict future health states, hypothetical sensor readings, and other aspects of a user's physiology or psychology. Analysis system 180 may also update and refine the predictive model based on new data generated by sensor array 110.

In particular embodiments, analysis system 180 may monitor disease-state progression and other health state changes over time. For example, analysis system 180 could continuously monitor a user's blood pressure over time to determine whether the user's hypertension is improving. Such monitoring may be used to identify trends and to generate alerts or predictions regarding possible health states. Similarly, analysis system 180 may also monitor data streams containing treatment or therapy information to determine whether the treatment or therapy is efficacious. For example, analysis system 180 could monitor a user's blood pressure over time to determine whether an ACE inhibitor treatment is affecting the user's hypertension.

In particular embodiments, analysis system 180 may monitor and analyze various data streams from a group of people to identify novel pre-disease states or risk states. For example, one or more sensor arrays 110 could monitor a plurality of users. As multiple users develop certain diseases, analysis system 180 could analyze data sets from these users prior to their development of the disease. The analysis of these data sets could allow analysis system 180 to identify certain health states that correlate with some level of risk for developing the disease.

Dyspnea, also called shortness of breath (SOB) or air hunger, is a debilitating symptom that is the experience of unpleasant or uncomfortable respiratory sensations. As used here, respiration refers the act or process of inhaling and exhaling, which may also be referred to as breathing or ventilation. Respiration rate refers to the rate a person breathes (e.g., breaths/minute). Respiratory minute volume refers to the volume of air that a person inhales and exhales over time (e.g., volume/minute). Dyspnea is a subjective experience of breathing discomfort that consists of qualitatively distinct sensations that vary in intensity. The experience derives from interactions among multiple physiological, psychological, behavioral, and environmental factors, and may induce secondary physiological and behavioral responses. Dyspnea on exertion may occur normally, but is considered indicative of disease when it occurs at a level of activity that is usually well tolerated. Dyspnea is different from tachypnea, hyperventilation, and hyperpnea, which refer to ventilatory parameters than can be objectively measured regardless of the person's subjective sensations.

Dyspnea is a common symptom of numerous medical disorders, particularly those involving the cardiovascular and respiratory systems. Dyspnea on exertion is the most common presenting complaint for people with respiratory impairment. However, dyspnea at rest is not uncommon. Dyspnea on exertion occurs when the left ventricular output fails to respond appropriately to increased activity or oxygen demand, with a resultant increase in pulmonary venous pressure. Dyspnea on exertion is not necessarily indicative of disease. Normal persons may feel dyspneic with strenuous exercise. The level of activity tolerated by any individual depends on such variables as age, sex, body weight, physical conditioning, attitude, and emotional motivation. Dyspnea on exertion is abnormal if it occurs with activity that is normally well tolerated by the person.

Spontaneous respiration (i.e., ventilation) is controlled by neural and chemical mechanisms. At rest, an average 70 kg person breathes 12 to 15 times a minute with a tidal volume of about 600 ml. A healthy individual is not aware of his or her respiratory effort until ventilation is doubled. Typically, dyspnea is not experienced until ventilation is tripled, and an abnormally increased muscular effort is consequently needed for the process of inspiration and expiration. Because dyspnea is a subjective experience, it does not always correlate with the degree of physiologic alteration. Some persons may complain of severe breathlessness with relatively minor physiologic change; others may deny breathlessness even with marked cardio-pulmonary deterioration.

Diagnosis of the cause of dyspnea may be made relatively easily in the presence of other clinical signs of heart or lung disease. Difficulty is sometimes encountered in determining the precipitating cause of breathlessness in a person with both cardiac and pulmonary conditions. An additional diagnostic problem may be the presence of anxiety or other emotional disorder. Diagnosis of the cause of dyspnea may require an analysis of physiological, psychological, behavioral, and environmental factors related to a person.

In general, dyspnea indicates that there is inadequate ventilation to sufficiently meet the body's needs. Dyspnea may be induced in four distinct settings: (1) increased ventilatory demand such as with exertion, febrile illness, hypoxic state, severe anemia, or metabolic acidosis; (2) decreased ventilatory capacity such as with pleural effusion, pneumothorax, intrathoracic mass, rib injury, or muscle weakness; (3) increased airway resistance such as with asthma or chronic obstructive pulmonary disease; and (4) decreased pulmonary compliance such as with interstitial fibrosis or pulmonary edema.

Although the exact mechanisms of dyspnea are not fully understood, some general principles are apparent. It is currently thought that there are three main components that contribute to dyspnea: afferent signals, efferent signals, and central information processing. It is believed that the central processing in the brain compares the afferent and efferent signals, and that a "mismatch" results in the sensation of dyspnea. In other words, dyspnea may result when the need for ventilation (afferent signaling) is not being met by the ventilation that is occurring (efferent signaling). Afferent signals are sensory neuronal signals that ascend to the brain. Afferent neurons significant in dyspnea arise from a large number of sources including the carotid bodies, medulla, lungs, and chest wall. Chemoreceptors in the carotid bodies and medulla supply information regarding the blood gas levels of $O_2$, $CO_2$ and $H^+$. In the lungs, juxtacapillary receptors are sensitive to pulmonary interstitial edema, while stretch receptors signal bronchoconstriction. Muscle spindles in the chest wall signal the stretch and tension of the respiratory muscles. Thus, poor ventilation leading to hypercapnia, left heart failure leading to interstitial edema (impairing gas exchange), asthma causing bronchoconstriction (limiting airflow), and muscle fatigue leading to ineffective respiratory muscle action could all contribute to a feeling of dyspnea. Efferent signals are the motor neuronal signals descending to the respiratory muscles. The primary respiratory muscle is the diaphragm. Other respiratory muscles include the external and internal intercostal muscles, the abdominal muscles and the accessory breathing muscles. As the brain receives afferent information relating to ventilation, it is able to compare it to the current level of respiration as determined by the efferent signals. If the level of respiration is inappropriate for the body's status then dyspnea might occur. There is a psychological component of dyspnea as well, as some people may become aware of their breathing in such circumstances but not experience the distress typical of dyspnea or experience more distress than the degree of ventilatory derangement would typically warrant.

In particular embodiments, sensor network 100 may analyze physiological, psychological, behavioral and environmental data steams to diagnose and monitor dyspnea in a user. In some embodiments, sensor array 110 may include one or more accelerometers and one or more respiration sensors. In other embodiments, sensor array 100 may include one or more pulse oximetry sensors and one or more respiration sensors. In yet other embodiments, sensor array 100 may include one or more accelerometers, one or more pulse oximetry sensors, and one or more respiration sensors. These sensors may be worn, carried, or otherwise affixed to the user. The accelerometers may measure and transmit information regarding the user's activity level. The respiration sensors may measure and transmit information regarding the user's breathing rate, volume, and intensity. As an example and not by way of limitation, a respiration sensor may measure a user's breathing rate in breaths/minute. As another example and not by way of limitation, a respiration sensor may measure a user's tidal volume in volume of air/breath. As yet another example and not by way of limitation, a respiration sensor may measure a user's respiration minute volume in volume of air/minute. As yet another example and not by way of limitation, a respiration sensor may measure a user's breathing amplitude. The pulse oximetry sensor may measure and transmit information regarding the oxygen saturation ($SpO_2$) of a user's blood. Sensor array 110 may transmit data streams containing acceleration, $SpO_2$, and respiration data of the user to analysis system 180, which may monitor and automatically detect changes in the user's activity and respiration.

In particular embodiments, analysis system 180 may analyze accelerometer, $SpO_2$, and respiration data from sensor array 110 to diagnose dyspnea in a user. As an example and not by way of limitation, respiration data may include a user's breathing rate, tidal volume, respiration minute volume, and breathing amplitude. A typical diagnostic test involves generating at least two data sets, wherein each set is collected from the user when he is engaged in different levels of activity. In particular embodiments, the first data set is collected from the user when he is resting, establishing the user's baseline respiration with no activity, and the second data set is collected from the user when he is engaged in a non-strenuous activity. A typical non-strenuous activity includes walking on a flat surface (e.g., a floor or treadmill) for several minutes. If the user's respiration increases to an abnormal level during the period of non-strenuous activity, this indicates dyspnea. Similarly, if the user's respiration increases but the user's $SpO_2$ does not increase, this indicates dyspnea. A higher respiration corresponds to more severe dyspnea. In one embodiment, the second data set may be collected when the user is engaged in a six-minute flat surface walk, wherein the user walks as far as possible for six minutes. If the person becomes out of breath or exhausted during the six-minute walk, this indicates dyspnea. The accuracy of diagnosis may generally be increased as the number of data sets is increased. Therefore, multiple data sets may be generated and analyzed to diagnose dyspnea in a user. Typically, the data sets will be collected from the user when he is engaged in varying levels of activity. Analysis system 180 may then create a model of the user's respiration with respect to activity, such as a graph or chart of activity versus respiration. Similarly, analysis system 180 may then create a model of the user's respiration with respect to $SpO_2$, such as a graph or chart of $SpO_2$ versus respiration. As an example and not by way of limitation, if a respiration sensor measures a user's breathing rate as 20 breaths/minute and pulse oximeter measures a user's $SpO_2$ at 95%, analysis system 180 may determine that the user's $SpO_2$ is abnormally low in comparison to the user's breathing rate and diagnose the user with dyspnea. As another example and not by way of limitation, if a respiration sensor measure a user's breathing rate as 26 breaths/minute, a pulse oximeter measures the user's $SpO_2$ at 95%, and an accelerometer measures the user hurrying on a level surface for several minutes, analysis system 180 may determine that the user's breathing rate is abnormally high in comparison to the user's activity and diagnose the user with dyspnea. Alternatively, analysis system 180 may determine the that user's $SpO_2$ is abnormally low in comparison to the user's breathing rate and diagnose the user with dyspnea.

In particular embodiments, analysis system 180 may reference the MRC Breathlessness Scale to assess the level of dyspnea in a person. The scale provides five different grades of dyspnea based on the circumstances in which it arises:

| Grade | Degree of Dyspnea |
|---|---|
| 0 | no dyspnea except with strenuous exercise |
| 1 | dyspnea when walking up an incline or hurrying on a level surface |
| 2 | dyspnea after 15 minutes of walking on a level surface |
| 3 | dyspnea after a few minutes of walking on a level surface |
| 4 | dyspnea with minimal activity such as getting dressed |

Analysis system 180 may also use variations of the MRC Breathlessness Scale, or other scales, both qualitative and quantitative, for assessing the severity of dyspnea in a person. For example, an alternative scale could grade dyspnea severity on a scale of 0 to 100, allowing for a more refined or a more precise diagnosis of a person's dyspnea.

In particular embodiments, analysis system 180 may analyze accelerometer, $SpO_2$, and respiration data from sensor array 110 to monitor the dyspnea grade of a user over time. Sensor array 110 may intermittently or continuously transmit information regarding the user's activity, $SpO_2$, and respiration over time to analysis system 180. Analysis system 180 may analyze one or more of these current data sets to determine the current dyspnea grade of the user. Analysis system 180 may then access accelerometer, pulse oximetry sensor, respiration sensor, and dyspnea grade data previously generated to compare it to current accelerometer, pulse oximetry sensor, respiration sensor, and dyspnea grade data of the user. Based on the comparison, analysis system 180 may then determine whether the user's dyspnea grade has changed over time. Analysis system 180 may also model the dyspnea grade with respect to time and identify any trends in dyspnea grade of the user. Based on these changes and trends in dyspnea grade, various alerts or warnings may be provided to the user or to a third-party (e.g., the user's physician).

In particular embodiments, sensor array 110 also includes a heart-rate sensor that may measure the user's heart-rate. Analysis system 180 may monitor a data stream containing this heart-rate data, allowing it to more accurately diagnose and monitor a user's dyspnea. For example, if a user is driving, an accelerometer may indicate the user is very active (based on the acceleration and deceleration of the vehicle), while a respiration sensor may indicate the user's respiration is relatively constant. In this case, based on only the respiration and accelerometer data, analysis system 180 may generate a false-negative diagnosis of dyspnea. By including a data stream containing information regarding the user's heart-rate (for example, that the user's heart-rate is steady while he is driving), analysis system 180 is less likely to generate a false-negative or false-positive dyspnea diagnosis.

In particular embodiments, sensor array 110 also includes an electromyograph that may measure the electrical potential generated by a user's muscle cells. These signals may be analyzed to detect muscle activity and medical abnormalities. Analysis system 180 may monitor a data stream containing this electromyograph data, allowing it to more accurately diagnose and monitor a user's dyspnea. In particular embodiments, an electromyograph may be used in place of an accelerometer to diagnose and monitor dyspnea in a user.

In particular embodiments, sensor array 110 also includes a kinesthetic sensor that may measure the position and posture of a user's body. Analysis system 180 may monitor a data stream containing this kinesthetic data, allowing it to more accurately diagnose and monitor a user's dyspnea.

In particular embodiments, sensor array 110 also includes an arterial blood gas sensor that may measure the pH of a user's blood, the partial pressure of $CO_2$ and $O_2$, and bicarbonate levels. Analysis system 180 may monitor a data stream containing this arterial blood gas data, allowing it to more accurately diagnose and monitor a user's dyspnea.

In particular embodiments, sensor array 110 also includes a user-input sensor that may receive information regarding a user's subjective experience of breathing discomfort. Analysis system 180 may monitor a data stream containing this information, allowing it to more accurately diagnose and monitor a user's dyspnea. For example, a user may subjectively feel breathing discomfort even though his ventilation appears to increase normally in response to activity. In this case, based on only respiration and accelerometer data, analysis system 180 may generate a false-negative diagnosis of dyspnea. By including in its analysis a data stream containing information regarding the user's subjective experience of breathing discomfort, analysis system 180 is less likely to generate a false-negative or false-positive dyspnea diagnosis. In one embodiment, a variation of mood sensor 400 may be used to receive information regarding a user's subjective experience of breathing discomfort. The user may input breathing discomfort, for example, on activity input widget 450. The user could then input an intensity of the breathing discomfort, for example, on mood intensity widget 440. Mood sensor 400 could then transmit a data stream based on this information to analysis system 180 for further analysis.

In particular embodiments, sensor array 110 also includes a user-input sensor that may receive information regarding treatments and therapies administered to the user. Analysis system 180 may monitor data streams containing treatment information to determine whether the treatment is affecting the user's dyspnea. For example, analysis system 180 could monitor a user's activity and respiration over time to determine whether an oral opioid treatment is affecting the user's dyspnea. Based on any changes or trends in the user's dyspnea grade that correlate with the treatment, various alerts or messages may be provided to the user or the user's physician.

Figure 10:
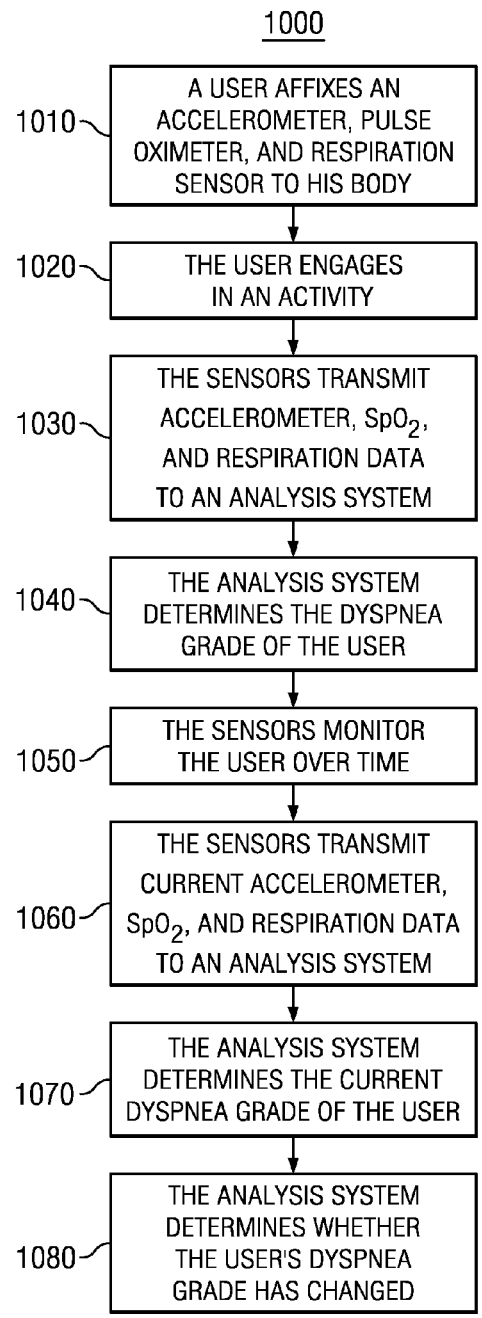
FIG. 10 illustrates an example method for detecting and monitoring dyspnea.

FIG. 10 illustrates an example method 1000 for diagnosing and monitoring dyspnea in a person. A user may affix one or more accelerometers, one or more pulse oximetry sensors, and one or more respiration sensors to his body at step 1010. Once affixed, the user may engage in one or more activities at step 1020. The sensors may measure the user's respiration, $SpO_2$ and activity, and transmit data streams based on these measurements to analysis system 180 at step 1030. Analysis system 180 may then analyze the respiration, $SpO_2$, and accelerometer data streams to determine the dyspnea grade of the user at step 1040. Over time, the sensors may continue to measure the user's respiration, $SpO_2$, and activity at step 1050. The sensors may transmit this current respiration, $SpO_2$, and activity data to analysis system 180 at step 1060. Analysis system 180 may then analyze the current respiration, $SpO_2$, and accelerometer data streams to determine the current dyspnea grade of the user at step 1070. Analysis system 180 may then access prior dyspnea grade data and compare it to the current dyspnea grade to determine if there are any changes or trends in the user's dyspnea grade at step 1080. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates particular components carrying out particular steps of the method of FIG. 10, this disclosure contemplates any suitable combination of any suitable components carrying out any suitable steps of the method of FIG. 10.

Musculoskeletal pathologies (or disorders) can affect a person's muscles, joints, tendons, ligaments. Musculoskeletal pathologies include dysfunctions and diseases of the skeletal muscles (e.g., muscle atrophies, muscular dystrophies, congenital myopathies) and diseases of the joints (e.g., arthritis).

Myopathy is an example of a muscular pathology in which a person's muscle fibers do not function properly, resulting in muscular dysfunction, such as weakness, spasticity, pain, cramping, or flaccidity. As used herein, the term "myopathy" is used broadly to reference both neuromuscular and musculoskeletal myopathies, including muscular dystrophy, myotonia, congenital myopathy, mitochondrial myopathy, familial periodic paralysis, inflammatory myopathy, metabolic myopathy, dermatomyositis, myalgia, myositis, rhabdomyolysis, and other acquired myopathies. Myopathies may be acquired, for example, from alcohol abuse or as a side-effect of statin treatment. Because different types of myopathies are caused by different pathways, there is no single treatment for myopathy. Treatments range from treatment of the symptoms to very specific cause-targeting treatments. Drug therapy, physical therapy, bracing for support, surgery, and even acupuncture are current treatments for a variety of myopathies.

Statins (HMG-CoA reductase inhibitors) are a class of drug used to lower a person's plasma cholesterol level. Statins are important drugs for lowering lipids (cholesterols), and have been found to correlate with lower rates of cardiac-events and cardiovascular mortality. Statins lower cholesterol by inhibiting HMG-CoA reductase, which is a rate-limiting enzyme of the mevalonate pathway of cholesterol synthesis. Inhibition of this enzyme in the liver results in decreased cholesterol synthesis as well as up regulation of LDL receptor synthesis, resulting in the increased clearance of low-density lipoprotein (LDL) from the bloodstream. There are both fermentation-derived and synthetically-derived statins. Statins include atorvastatin, cerivastatin, fluvastatin, lovastatin, mevastatin, pitavastatin, pravastatin, rosuvastatin, and simvastatin. There are also several combination therapies that include statins. These combination therapies include Vytorin (simvastatin and ezetimibe), Advicor (lovastatin and niacin), Caduet (atorvastatin and amlodipine besylate), and Simcor (simvastatin and niacin).

Statins are generally well-tolerated by patients. The most common adverse side effects are elevated liver enzymes levels and muscle-related complaints. Other statin side-effects include gastrointestinal issues, liver enzyme derangements, cognitive dysfunction, hair loss, and polyneuropathy. A more serious but rare statin side-effect is rhabdomyolysis leading to acute renal failure. Symptoms of statin-induced myopathy include fatigue, muscle pain, muscle tenderness, muscle weakness, muscle cramping, and tendon pain. The muscle symptoms tend to be proximal, symmetrical, generalized, and worse with exercise.

In general, skeletal muscular damage correlates with increased levels of circulating creatine phosphokinase. Damaged muscle cells may rupture and release creatine phosphokinase. Current guidelines define myositis as muscle discomfort with a creatine phosphokinase level above ten times the upper limit of normal. However, some studies show that a person may still experience statin-based myopathy even though the person has normal or moderately elevated creatine phosphokinase levels. One theory is that statin-induced myopathy may cause microscopic muscle damage that is not sufficient to break the cell open and cause a release of creatinine phosphokinase into the blood. Consequently, statins may cause ongoing damage to the muscle at the microscopic level that is not revealed in the blood tests used to check for muscle damage. An alternate theory is that statins induce mitochondrial dysfunction, which may not be associated with creatine phosphokinase release from muscle cells.

The mechanisms of statin-induced myopathy are unknown. One proposal is that impaired synthesis of cholesterol leads to changes in the cholesterol in myocyte membranes that change the behavior of the membrane. However, inherited disorders of the cholesterol synthesis pathway that reduce cholesterol concentrations are not associated with myopathy. Another proposed mechanism is that impaired synthesis of compounds in the cholesterol pathway, particularly coenzyme Q10, could lead to impaired enzyme activity in mitochondria. Although low serum concentrations of coenzyme Q10 have been noted in patients taking statins, concentrations in muscle have not consistently shown this pattern. A third proposed mechanism is depletion of isoprenoids-lipids that are a product of the hydroxymethyl glutaryl coenzyme A reductase pathway and that prevent myofibre apoptosis. A fourth proposed mechanism is that some patients have a genetic predisposition for statin-induced myopathy. A common variation in the SLCO1B1 gene has been correlated with a significant increase in the risk of myopathy, though the mechanism behind this increased risk is not known. Statin-induced myopathy in a person may be caused by one or more of the above mechanisms, or a yet unidentified mechanism.

Statin-induced myopathy may be treated using a variety of methods. One treatment is to simply lower a patient's statin dose to the lowest dose required to achieve lipid management goals. As used herein, "dose" refers to both the amount and frequency of a drug administered to a patient. This treatment is based on the clinical observation that the severity of myopathy typically correlates with increased statin dosage. Another treatment is to change the type of statin to a statin that presents a lower myopathy risk. This treatment is based on the theory that the risk of myopathy among statins may vary based on their water solubility, and that more hydrophilic statins may have less muscle penetration. Therefore, a patient experiencing statin-induced myopathy with a fat-soluble statin (e.g., simvastatin, rosuvastatin, atorvastatin) may change to a water-soluble statin (e.g., pravastatin, fluvastatin). However, some studies suggest that there is no clinical or epidemiological evidence supporting the differentiation of statin myotoxicity potential based on hydrophilicity. The potency of the statin also seems to be correlated with the risk of myopathy, with the more potent stains having greater risk. Yet another treatment is to prescribe coenzyme Q10 supplements. This treatment is based on the theory that statin treatment inhibits the synthesis of coenzyme Q10 (ubiquinone). However, the efficacy of this treatment is unclear. A variety of other treatments are also possible for statin-induced myopathy, and the examples described above are not intended to be limiting.

In particular embodiments, sensor network 100 may analyze physiological, psychological, behavioral and environmental data steams to diagnose and monitor a musculoskeletal pathology in a user. In particular embodiments, the musculoskeletal pathology is myopathy. In particular embodiments, sensor array 110 may include one or more accelerometers. In particular embodiments, sensor array 100 may also include one or more kinesthetic sensors. These sensors may be worn, carried, or otherwise affixed to the user. The accelerometers may measure and transmit information regarding the user's activity level and range of motion. The kinesthetic sensors may measure and transmit information regarding the position and posture of the user's body. Sensor array 110 may transmit data streams containing acceleration data and kinesthetic data of the user to analysis system 180, which may monitor and automatically detect changes in the user's activity level, position, and range of motion. Sensor array 110 may also monitor and detect patterns of motion in a user.

In particular embodiments, analysis system 180 may analyze accelerometer data and/or kinesthetic data from sensor array 110 to diagnose a musculoskeletal pathology, such as myopathy, in a user. A typical diagnostic test involves generating at least two data sets, wherein each set is collected from the user during different time periods. As an example and not by way of limitation, statin-based myopathy may be diagnosed by collecting data before and after a patient has used a statin treatment. A first data set may be collected from the user prior to beginning statin treatment, establishing the user's baseline activity level and range of motion, and a second data set may be collected from the user while he is undergoing statin treatment. If the user's activity level or range of motion decreases while he is undergoing statin treatment, this indicates statin-induced myopathy. A larger decrease in activity level or range of motion corresponds to more severe myopathy. As another example and not by way of limitation, the first and second data sets may both be collected from the user while he is undergoing statin treatment, but at different stages of treatment. For example, the first data set may be generated while the user is taking a first type of statin and the second data set may be generated while the user is taking a second type of statin. The accuracy of diagnosis may generally be increased as the number of data sets is increased. Therefore, multiple data sets may be generated and analyzed to diagnose myopathy in a user. Typically, the data sets will be collected from the user during different time periods while he is undergoing statin treatment. Analysis system 180 may then create a model of the user's myopathy with respect to activity level and range of motion, such as a graph for chart of activity level or range of motion over time. Although this disclosure describes diagnosing particular types of musculoskeletal pathologies, this disclosure contemplates diagnosing any suitable types of musculoskeletal pathologies. Moreover, although this disclosure describes collecting data sets at particular time periods, this disclosure contemplates collecting data sets at any suitable time periods.

The degree of musculoskeletal pathology can be assessed both by the number of symptoms present and their intensity. Analysis system 180 may use a variety of scales, both qualitative and quantitative, for assessing the severity of musculoskeletal pathology in a person. As an example and not by way of limitation, a user may report both muscle pain and weakness. A simple five point scale may be devised to quantitate the intensity of the various symptoms. Another user may report muscle cramping and weakness and yet another user may report all three symptoms. Each symptom may be scored for intensity and then algorithmically combined into a composite scale that could describe the degree of musculoskeletal pathology. As an example and not by way of limitation, a scale could grade musculoskeletal pathology severity on a scale of 0 to 100, wherein 0 is no activity level or range of motion degradation and 100 is severe muscle pain with any movement. Analysis system 180 may also use different scales for different types of musculoskeletal pathology. As an example and not by way of limitation, a first scale could be used to grade myopathy severity, and a second scale could be used to grade arthritis severity.

In particular embodiments, analysis system 180 may analyze accelerometer data and/or kinesthetic data from sensor array 110 to monitor the musculoskeletal pathology grade of a user over time. Sensor array 110 may intermittently or continuously transmit information regarding the user's activity level and range of motion over time to analysis system 180. Analysis system 180 may analyze one or more of these current data sets to determine the current musculoskeletal pathology grade of the user. Analysis system 180 may then access accelerometer, kinesthetic sensor, and musculoskeletal pathology grade data previously generated to compare it to current accelerometer, kinesthetic sensor, and musculoskeletal pathology grade data of the user. Based on the comparison, analysis system 180 may then determine whether the user's musculoskeletal pathology grade has changed over time. Analysis system 180 may also model the musculoskeletal pathology grade with respect to time and identify any trends in musculoskeletal pathology grade of the user. Based on these changes and trends in musculoskeletal pathology grade, various alerts or warnings may be provided to the user or to a third-party (e.g., the user's physician).

In particular embodiments, sensor array 110 also includes a user-input sensor that may receive information regarding a user's muscle complaints. Analysis system 180 may monitor a data stream containing this information, allowing it to more accurately diagnose and monitor a user's musculoskeletal pathology. For example, a user may feel muscle pain even though his activity level and range of motion appear unchanged with treatment. In this case, based on only accelerometer or kinesthetic data, analysis system 180 may generate a false-negative diagnosis of a musculoskeletal pathology. By including in its analysis a data stream containing information regarding the user's muscle complaints, analysis system 180 is less likely to generate a false-negative or false-positive diagnosis. In one embodiment, a variation of mood sensor 400 may be used to receive information regarding a user's muscle complaints. The user may input the type of muscle complaint, for example, on activity input widget 450. Muscle complaints could include fatigue, muscle pain, muscle tenderness, muscle weakness, muscle cramping, and tendon pain. The user could then input an intensity of the muscle complaint, for example, on mood intensity widget 440. Mood sensor 400 could then transmit a data stream based on this information to analysis system 180 for further analysis.

In particular embodiments, sensor array 110 also includes a user-input sensor that may receive information regarding treatments administered to the user, such as the type and dose of statin treatment administered to the user. Analysis system 180 may monitor data streams containing treatment information to determine whether the treatment is affecting the user's statin-induced myopathy. For example, analysis system 180 could monitor a user's activity level and range of motion over time to determine whether the statin is causing myopathy. Based on any changes or trends in the user's activity level or range of motion that correlate with the statin treatment, various alerts or messages may be provided to the user or the user's physician. In particular embodiments, the prescribing physician may change or modify the user's statin treatment in response to any changes or trends in the user's myopathy. For example, if the user's myopathy is worsening, the user's physician may prescribe a lower dose statin treatment, prescribe a different type of statin, or prescribe a different class of medication. In alternative embodiments, sensor array 110 may include a data feed that transmits information regarding treatments administered to the user. Although this disclosure describes receiving information regarding particular types of treatments for particular types of musculoskeletal pathologies, this disclosure contemplates receiving information regarding any suitable types of treatments for any suitable types of musculoskeletal pathologies.

In particular embodiments, sensor array 110 also includes an electromyograph that may measure the electrical potential generated by a user's muscle cells. These signals may be analyzed to detect muscle activity and medical abnormalities. Analysis system 180 may monitor a data stream containing this electromyograph data, allowing it to more accurately diagnose and monitor a user's musculoskeletal pathologies. In particular embodiments, an electromyograph may be used in place of or in addition to an accelerometer to diagnose and monitor musculoskeletal pathologies in a user.

Figure 11:
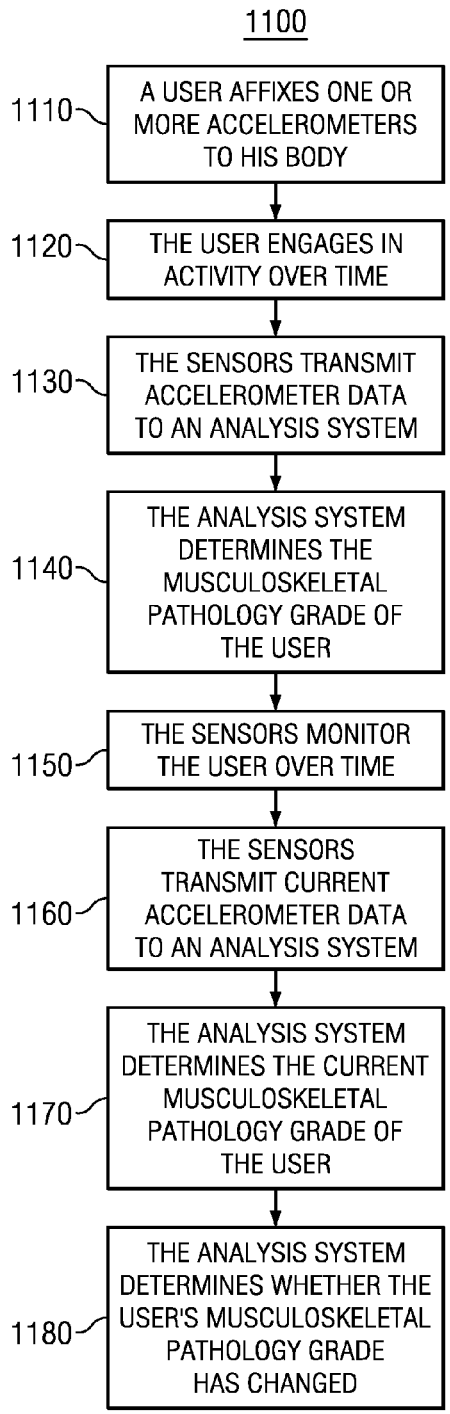
FIG. 11 illustrates an example method for detecting and monitoring musculoskeletal pathology.

FIG. 11 illustrates an example method 1100 for diagnosing and monitoring musculoskeletal pathology in a person. A user may affix one or more accelerometers to his body at step 1110. In particular embodiments, the user may affix one or more kinesthetic sensors to his body at step 1110 in addition to or instead of the one or more accelerometers. Once affixed, the user may engage in one or more activities over time at step 1120. The sensors may measure the user's activity level and range of motion, and transmit data streams based on these measurements to analysis system 180 at step 1130. Analysis system 180 may then analyze the accelerometer data streams (and/or the kinesthetic data streams) to determine the musculoskeletal pathology grade of the user at step 1140. Over time, the sensors may continue to measure the user's activity level and range of motion at step 1150. The sensors may transmit this current activity level and range of motion data to analysis system 180 at step 1160. Analysis system 180 may then analyze the current accelerometer data streams (and/or the kinesthetic data streams) to determine the current musculoskeletal pathology grade of the user at step 1170. Analysis system 180 may then access prior musculoskeletal pathology grade data and compare it to the current musculoskeletal pathology grade to determine if there are any changes or trends in the user's musculoskeletal pathology grade at step 1180. Although this disclosure describes and illustrates particular steps of the method of FIG. 11 as occurring in a particular order, this disclosure contemplates any suitable steps of the method of FIG. 11 occurring in any suitable order. Moreover, although this disclosure describes and illustrates particular components carrying out particular steps of the method of FIG. 11, this disclosure contemplates any suitable combination of any suitable components carrying out any suitable steps of the method of FIG. 11.

While this disclosure has focused on statin-induced myopathy, this disclosure is intended to encompass the diagnosis and monitoring of any type of musculoskeletal pathology. One of ordinary skill in the art would recognize that the embodiments disclosed herein may be used to diagnosis and monitor a variety of musculoskeletal pathologies, such as, for example arthritis, muscular dystrophy, myotonia, congenital myopathy, mitochondrial myopathy, familial periodic paralysis, inflammatory myopathy, metabolic myopathy, dermatomyositis, myalgia, myositis, rhabdomyolysis, and other acquired myopathies.

Display system 190 may render, visualize, display, message, notify, and publish to one or more users based on the one or more analysis outputs from analysis system 180. An analysis output from analysis system 180 may be transmitted to display system 190 over any suitable medium. Display system 190 may include any suitable I/O device that may enable communication between a person and display system 190. For example, display system 190 may include a video monitor, speaker, vibrator, touch screen, printer, another suitable I/O device or a combination of two or more of these. Display system 190 may be any computing device with a suitable I/O device, such as computer system 1400.

Display system 190 comprises one or more local display systems 130 and/or one or more remote display systems 140. Where display system 190 comprises multiple subsystems (e.g., local display systems 130 and remote display systems 140), display of analysis outputs may occur on one or more subsystems. In one embodiment, local display systems 130 and remote display systems 140 may present identical displays based on the analysis output. In another embodiment, local display systems 130 and remote display systems 140 may present different displays based on the analysis output.

In particular embodiments, a user-input sensor in sensor array 110 may also function as display system 190. Any client system with a suitable I/O device may serve as a user-input sensor and display system 190. For example, a smart phone with a touch screen may function both as a user-input sensor and as display system 190.

Display system 190 may display an analysis output in real-time as it is received from analysis system 180. In particular embodiments, real-time analysis of data streams from sensor array 110 by analysis system 180 allows the user to receive real-time information about his health status. It is also possible for the user to receive real-time feedback from display system 190 (e.g., warnings about health risks, recommending therapies, etc.).

One of ordinary skill in the art would recognize that display system 190 could perform a variety of display-related processes using a variety of techniques and that the example embodiments disclosed herein are not meant to be limiting.

In particular embodiments, display system 190 may render and visualize data based on analysis output from analysis system 180. Display system 190 may render and visualize using any suitable means, including computer system 1400 with a suitable I/O device, such as a video monitor, speaker, touch screen, printer, another suitable I/O device or a combination of two or more of these.

Rendering is the process of generating an image from a model. The model is a description of an object in a defined language or data structure. A description may include color, size, orientation, geometry, viewpoint, texture, lighting, shading, and other object information. The rendering may be any suitable image, such as a digital image or raster graphics image. Rendering may be performed on any suitable computing device.

Visualization is the process of creating images, diagrams, or animations to communicate information to a user. Visualizations may include diagrams, images, objects, graphs, charts, lists, maps, text, etc. Visualization may be performed on any suitable device that may present information to a user, including a video monitor, speaker, touch screen, printer, another suitable I/O device or a combination of two or more of these.

In particular embodiments, rendering may be performed partially on analysis system 180 and partially on display system 190. In other embodiments, rendering is completely performed on analysis system 180, while visualization is performed on display system 190.

In particular embodiments, display system 190 may message, notify, and publish data based on analysis output from analysis system 180. Display system 190 may message and publish using any suitable means, including email, instant message, text message, audio message, page, MMS text, social network message, another suitable messaging or publishing means, or a combination of two or more of these.

In particular embodiments, display system 190 may publish some or all of the analysis output such that the publication may be viewed by one or more third-parties. In one embodiment, display system 190 may automatically publish the analysis output to one or more websites. For example, a user of mood sensor 400 may automatically have their inputs into the sensor published to social networking sites (e.g., Facebook, Twitter, etc.).

In particular embodiments, display system 190 may send or message some or all of the analysis output to one or more third-parties. In one embodiment, display system 190 may automatically send the analysis output to one or more healthcare providers. For example, a user wearing a portable blood glucose monitor may have all of the data from that sensor transmitted to his doctor. In another embodiment, display system 190 will only send the analysis output to a healthcare provider when one or more threshold criteria are met. For example, a user wearing a portable blood glucose monitor may not have any data from that sensor transmitted to his doctor unless his blood glucose data shows that he is severely hypoglycemic (e.g., below 2.8 mmol/l). In particular embodiments, display system 190 may message one or more alerts to a user or third-party based on the analysis output. An alert may contain a notice, warning, or recommendation for the user or third-party. For example, a user wearing a blood glucose monitor may receive an alert if his blood glucose level shows that he is moderately hypoglycemic (e.g., below 3.5 mmol/l) warning of the hypoglycemia and recommending that he eat something.

In particular embodiments, display system 190 may display one or more therapies to a user based on analysis output from analysis system 180. In particular embodiments, these are recommended therapies for the user. In other embodiments, these are therapeutic feedbacks that provide a direct therapeutic benefit to the user. Display system 190 may deliver a variety of therapies, such as interventions, biofeedback, breathing exercises, progressive muscle relaxation exercises, physical therapy, presentation of personal media (e.g., music, personal pictures, etc.), offering an exit strategy (e.g., calling the user so he has an excuse to leave a stressful situation), references to a range of psychotherapeutic techniques, and graphical representations of trends (e.g., illustrations of health metrics over time), cognitive reframing therapy, and other therapeutic feedbacks. Display system 190 may also provide information on where the user can seek other therapies, such as specific recommendations for medical care providers, hospitals, etc.

In particular embodiments, display system 190 may transform, select, or represent one or more data streams or analysis outputs with an implicit or explicit geometric structure, to allow the exploration, analysis and understanding of the data.

In particular embodiments, a user may modify the visualization in real-time, thus affording perception of patterns and structural relations in the data streams or analysis outputs presented by display system 190.

Figure 12:
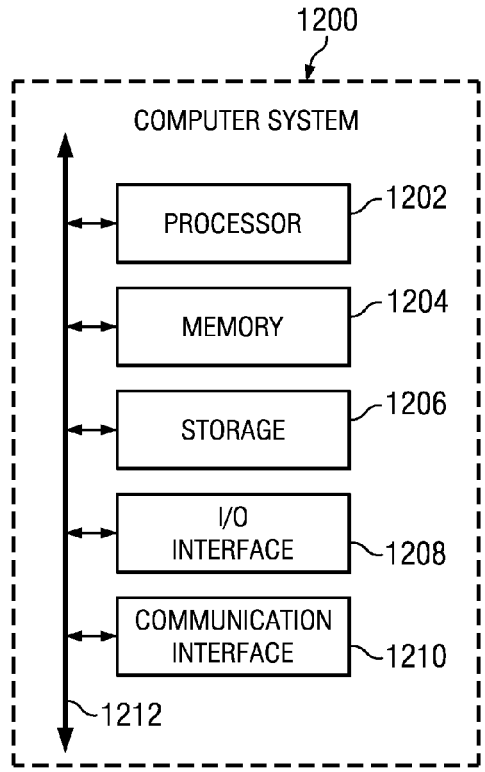
FIG. 12 illustrates an example computer system.

FIG. 12 illustrates an example computer system 1200. In particular embodiments, one or more computer systems 1200 perform one or more steps of one or more methods described or illustrated herein. In particular embodiments, one or more computer systems 1200 provide functionality described or illustrated herein. In particular embodiments, software running on one or more computer systems 1200 performs one or more steps of one or more methods described or illustrated herein or provides functionality described or illustrated herein. Particular embodiments include one or more portions of one or more computer systems 1200.

This disclosure contemplates any suitable number of computer systems 1200. This disclosure contemplates computer system 1200 taking any suitable physical form. As example and not by way of limitation, computer system 1200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1200 may include one or more computer systems 1200; be unitary or distributed; span multiple locations; span multiple machines; span multiple data centers; or reside in a cloud, which may include one or more cloud components in one or more networks. Where appropriate, one or more computer systems 1200 may perform without substantial spatial or temporal limitation one or more steps of one or more methods described or illustrated herein. As an example and not by way of limitation, one or more computer systems 1200 may perform in real time or in batch mode one or more steps of one or more methods described or illustrated herein. One or more computer systems 1200 may perform at different times or at different locations one or more steps of one or more methods described or illustrated herein, where appropriate.

In particular embodiments, computer system 1200 includes a processor 1202, memory 1204, storage 1206, an input/output (I/O) interface 1208, a communication interface 1210, and a bus 1212. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1202 includes hardware for executing instructions, such as those making up a computer program. As an example and not by way of limitation, to execute instructions, processor 1202 may retrieve (or fetch) the instructions from an internal register, an internal cache, memory 1204, or storage 1206; decode and execute them; and then write one or more results to an internal register, an internal cache, memory 1204, or storage 1206. In particular embodiments, processor 1202 may include one or more internal caches for data, instructions, or addresses. This disclosure contemplates processor 1202 including any suitable number of any suitable internal caches, where appropriate. As an example and not by way of limitation, processor 1202 may include one or more instruction caches, one or more data caches, and one or more translation lookaside buffers (TLBs). Instructions in the instruction caches may be copies of instructions in memory 1204 or storage 1206, and the instruction caches may speed up retrieval of those instructions by processor 1202. Data in the data caches may be copies of data in memory 1204 or storage 1206 for instructions executing at processor 1202 to operate on; the results of previous instructions executed at processor 1202 for access by subsequent instructions executing at processor 1202 or for writing to memory 1204 or storage 1206; or other suitable data. The data caches may speed up read or write operations by processor 1202. The TLBs may speed up virtual-address translation for processor 1202. In particular embodiments, processor 1202 may include one or more internal registers for data, instructions, or addresses. This disclosure contemplates processor 1202 including any suitable number of any suitable internal registers, where appropriate. Where appropriate, processor 1202 may include one or more arithmetic logic units (ALUs); be a multi-core processor; or include one or more processors 1202. Although this disclosure describes and illustrates a particular processor, this disclosure contemplates any suitable processor.

In particular embodiments, memory 1204 includes main memory for storing instructions for processor 1202 to execute or data for processor 1202 to operate on. As an example and not by way of limitation, computer system 1200 may load instructions from storage 1206 or another source (such as, for example, another computer system 1200) to memory 1204. Processor 1202 may then load the instructions from memory 1204 to an internal register or internal cache. To execute the instructions, processor 1202 may retrieve the instructions from the internal register or internal cache and decode them. During or after execution of the instructions, processor 1202 may write one or more results (which may be intermediate or final results) to the internal register or internal cache. Processor 1202 may then write one or more of those results to memory 1204. In particular embodiments, processor 1202 executes only instructions in one or more internal registers or internal caches or in memory 1204 (as opposed to storage 1206 or elsewhere) and operates only on data in one or more internal registers or internal caches or in memory 1204 (as opposed to storage 1206 or elsewhere). One or more memory buses (which may each include an address bus and a data bus) may couple processor 1202 to memory 1204. Bus 1212 may include one or more memory buses, as described below. In particular embodiments, one or more memory management units (MMUs) reside between processor 1202 and memory 1204 and facilitate accesses to memory 1204 requested by processor 1202. In particular embodiments, memory 1204 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1204 may include one or more memories 1204, where appropriate. Although this disclosure describes and illustrates particular memory, this disclosure contemplates any suitable memory.

In particular embodiments, storage 1206 includes mass storage for data or instructions. As an example and not by way of limitation, storage 1206 may include an HDD, a floppy disk drive, flash memory, an optical disc, a magneto-optical disc, magnetic tape, or a Universal Serial Bus (USB) drive or a combination of two or more of these. Storage 1206 may include removable or non-removable (or fixed) media, where appropriate. Storage 1206 may be internal or external to computer system 1200, where appropriate. In particular embodiments, storage 1206 is non-volatile, solid-state memory. In particular embodiments, storage 1206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1206 taking any suitable physical form. Storage 1206 may include one or more storage control units facilitating communication between processor 1202 and storage 1206, where appropriate. Where appropriate, storage 1206 may include one or more storages 1206. Although this disclosure describes and illustrates particular storage, this disclosure contemplates any suitable storage.

In particular embodiments, I/O interface 1208 includes hardware, software, or both providing one or more interfaces for communication between computer system 1200 and one or more I/O devices. Computer system 1200 may include one or more of these I/O devices, where appropriate. One or more of these I/O devices may enable communication between a person and computer system 1200. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1208 for them. Where appropriate, I/O interface 1208 may include one or more device or software drivers enabling processor 1202 to drive one or more of these I/O devices. I/O interface 1208 may include one or more I/O interfaces 1208, where appropriate. Although this disclosure describes and illustrates a particular I/O interface, this disclosure contemplates any suitable I/O interface.

In particular embodiments, communication interface 1210 includes hardware, software, or both providing one or more interfaces for communication (such as, for example, packet-based communication) between computer system 1200 and one or more other computer systems 1200 or one or more networks. As an example and not by way of limitation, communication interface 1210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1210 for it. As an example and not by way of limitation, computer system 1200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1200 may include any suitable communication interface 1210 for any of these networks, where appropriate. Communication interface 1210 may include one or more communication interfaces 1210, where appropriate. Although this disclosure describes and illustrates a particular communication interface, this disclosure contemplates any suitable communication interface.

In particular embodiments, bus 1212 includes hardware, software, or both coupling components of computer system 1200 to each other. As an example and not by way of limitation, bus 1212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (USA) bus, an INFINIBAND interconnect, a low-pin-count (LPC) bus, a memory bus, a Micro Channel Architecture (MCA) bus, a Peripheral Component Interconnect (PCI) bus, a PCI-Express (PCI-X) bus, a serial advanced technology attachment (SATA) bus, a Video Electronics Standards Association local (VLB) bus, or another suitable bus or a combination of two or more of these. Bus 1212 may include one or more buses 1212, where appropriate. Although this disclosure describes and illustrates a particular bus, this disclosure contemplates any suitable bus or interconnect.

Herein, reference to a computer-readable storage medium encompasses one or more non-transitory, tangible computer-readable storage media possessing structure. As an example and not by way of limitation, a computer-readable storage medium may include a semiconductor-based or other integrated circuit (IC) (such, as for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. Herein, reference to a computer-readable storage medium excludes any medium that is not eligible for patent protection under 35 U.S.C. §101. Herein, reference to a computer-readable storage medium excludes transitory forms of signal transmission (such as a propagating electrical or electromagnetic signal per se) to the extent that they are not eligible for patent protection under 35 U.S.C. §101. A computer-readable non-transitory storage medium may be volatile, non-volatile, or a combination of volatile and non-volatile, where appropriate.

This disclosure contemplates one or more computer-readable storage media implementing any suitable storage. In particular embodiments, a computer-readable storage medium implements one or more portions of processor 1202 (such as, for example, one or more internal registers or caches), one or more portions of memory 1204, one or more portions of storage 1206, or a combination of these, where appropriate. In particular embodiments, a computer-readable storage medium implements RAM or ROM. In particular embodiments, a computer-readable storage medium implements volatile or persistent memory. In particular embodiments, one or more computer-readable storage media embody software. Herein, reference to software may encompass one or more applications, bytecode, one or more computer programs, one or more executables, one or more instructions, logic, machine code, one or more scripts, or source code, and vice versa, where appropriate. In particular embodiments, software includes one or more application programming interfaces (APIs). This disclosure contemplates any suitable software written or otherwise expressed in any suitable programming language or combination of programming languages. In particular embodiments, software is expressed as source code or object code. In particular embodiments, software is expressed in a higher-level programming language, such as, for example, C, Perl, or a suitable extension thereof. In particular embodiments, software is expressed in a lower-level programming language, such as assembly language (or machine code). In particular embodiments, software is expressed in JAVA. In particular embodiments, software is expressed in Hyper Text Markup Language (HTML), Extensible Markup Language (XML), or other suitable markup language.

Figure 13:
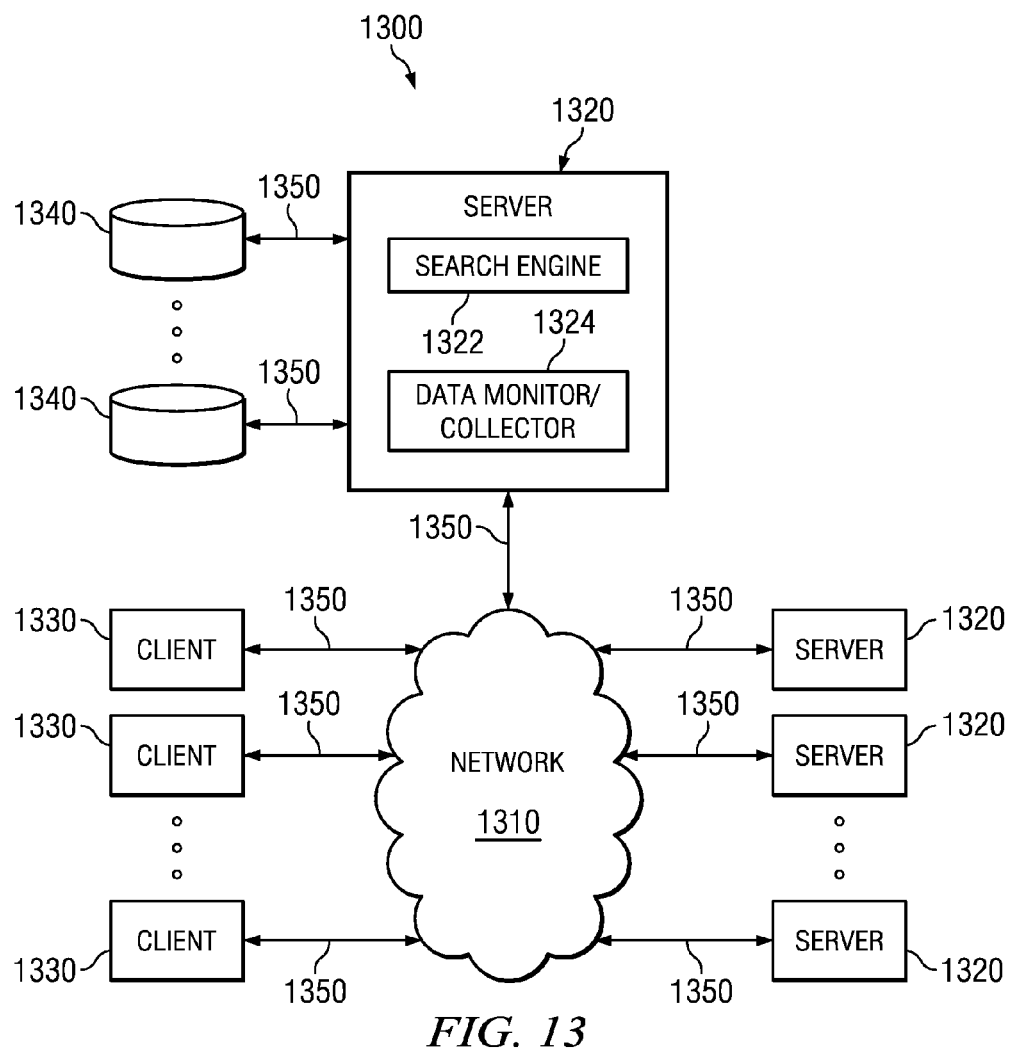
FIG. 13 illustrates an example network environment.

FIG. 13 illustrates an example network environment 1300. This disclosure contemplates any suitable network environment 1300. As an example and not by way of limitation, although this disclosure describes and illustrates a network environment 1300 that implements a client-server model, this disclosure contemplates one or more portions of a network environment 1300 being peer-to-peer, where appropriate. Particular embodiments may operate in whole or in part in one or more network environments 1300. In particular embodiments, one or more elements of network environment 1300 provide functionality described or illustrated herein. Particular embodiments include one or more portions of network environment 1300. Network environment 1300 includes a network 1310 coupling one or more servers 1320 and one or more clients 1330 to each other. This disclosure contemplates any suitable network 1310. As an example and not by way of limitation, one or more portions of network 1310 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 1310 may include one or more networks 1310.

Links 1350 couple servers 1320 and clients 1330 to network 1310 or to each other. This disclsoure contemplates any suitable links 1350. As an example and not by way of limitation, one or more links 1350 each include one or more wireline (such as, for example, Digital Subscriber Line (DSL) or Data Over Cable Service Interface Specification (DOCSIS)), wireless (such as, for example, Wi-Fi or Worldwide Interoperability for Microwave Access (WiMAX)) or optical (such as, for example, Synchronous Optical Network (SONET) or Synchronous Digital Hierarchy (SDH)) links 1350. In particular embodiments, one or more links 1350 each includes an intranet, an extranet, a VPN, a LAN, a WLAN, a WAN, a MAN, a communications network, a satellite network, a portion of the Internet, or another link 1350 or a combination of two or more such links 1350. Links 1350 need not necessarily be the same throughout network environment 1300. One or more first links 1350 may differ in one or more respects from one or more second links 1350.

This disclosure contemplates any suitable servers 1320. As an example and not by way of limitation, one or more servers 1320 may each include one or more advertising servers, applications servers, catalog servers, communications servers, database servers, exchange servers, fax servers, file servers, game servers, home servers, mail servers, message servers, news servers, name or DNS servers, print servers, proxy servers, sound servers, standalone servers, web servers, or web-feed servers. In particular embodiments, a server 1320 includes hardware, software, or both for providing the functionality of server 1320. As an example and not by way of limitation, a server 1320 that operates as a web server may be capable of hosting websites containing web pages or elements of web pages and include appropriate hardware, software, or both for doing so. In particular embodiments, a web server may host HTML or other suitable files or dynamically create or constitute files for web pages on request. In response to a Hyper Text Transfer Protocol (HTTP) or other request from a client 1330, the web server may communicate one or more such files to client 1330. As another example, a server 1320 that operates as a mail server may be capable of providing e-mail services to one or more clients 1330. As another example, a server 1320 that operates as a database server may be capable of providing an interface for interacting with one or more data stores (such as, for example, data stores 1340 described below). Where appropriate, a server 1320 may include one or more servers 1320; be unitary or distributed; span multiple locations; span multiple machines; span multiple datacenters; or reside in a cloud, which may include one or more cloud components in one or more networks.

In particular embodiments, one or more links 1350 may couple a server 1320 to one or more data stores 1340. A data store 1340 may store any suitable information, and the contents of a data store 1340 may be organized in any suitable manner. As an example and not by way or limitation, the contents of a data store 1340 may be stored as a dimensional, flat, hierarchical, network, object-oriented, relational, XML, or other suitable database or a combination or two or more of these. A data store 1340 (or a server 1320 coupled to it) may include a database-management system or other hardware or software for managing the contents of data store 1340. The database-management system may perform read and write operations, delete or erase data, perform data deduplication, query or search the contents of data store 1340, or provide other access to data store 1340.

In particular embodiments, one or more servers 1320 may each include one or more search engines 1322. A search engine 1322 may include hardware, software, or both for providing the functionality of search engine 1322. As an example and not by way of limitation, a search engine 1322 may implement one or more search algorithms to identify network resources in response to search queries received at search engine 1322, one or more ranking algorithms to rank identified network resources, or one or more summarization algorithms to summarize identified network resources. In particular embodiments, a ranking algorithm implemented by a search engine 1322 may use a machine-learned ranking formula, which the ranking algorithm may obtain automatically from a set of training data constructed from pairs of search queries and selected Uniform Resource Locators (URLs), where appropriate.

In particular embodiments, one or more servers 1320 may each include one or more data monitors/collectors 1324. A data monitor/collection 1324 may include hardware, software, or both for providing the functionality of data collector/collector 1324. As an example and not by way of limitation, a data monitor/collector 1324 at a server 1320 may monitor and collect network-traffic data at server 1320 and store the network-traffic data in one or more data stores 1340. In particular embodiments, server 1320 or another device may extract pairs of search queries and selected URLs from the network-traffic data, where appropriate.

This disclosure contemplates any suitable clients 1330. A client 1330 may enable a user at client 1330 to access or otherwise communicate with network 1310, servers 1320, or other clients 1330. As an example and not by way of limitation, a client 1330 may have a web browser, such as MICROSOFT INTERNET EXPLORER or MOZILLA FIREFOX, and may have one or more add-ons, plug-ins, or other extensions, such as GOOGLE TOOLBAR or YAHOO TOOLBAR. A client 1330 may be an electronic device including hardware, software, or both for providing the functionality of client 1330. As an example and not by way of limitation, a client 1330 may, where appropriate, be an embedded computer system, an SOC, an SBC (such as, for example, a COM or SOM), a desktop computer system, a laptop or notebook computer system, an interactive kiosk, a mainframe, a mesh of computer systems, a mobile telephone, a PDA, a netbook computer system, a server, a tablet computer system, or a combination of two or more of these. Where appropriate, a client 1330 may include one or more clients 1330; be unitary or distributed; span multiple locations; span multiple machines; span multiple datacenters; or reside in a cloud, which may include one or more cloud components in one or more networks.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context. Furthermore, "a", "an," or "the" is intended to mean "one or more," unless expressly indicated otherwise or indicated otherwise by context. Therefore, herein, "an A" or "the A" means "one or more A," unless expressly indicated otherwise or indicated otherwise by context.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, this disclosure encompasses any suitable combination of one or more features from any example embodiment with one or more features of any other example embodiment herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A method comprising, by one or more computing devices:
    generating a display for presentation to a user, the display comprising an avatar of a person's body in three spatial dimensions, the avatar being configured to receive one or more inputs from the user;
    receiving a first input from the user identifying a type of a physiological event;
    receiving a second input from the user identifying a location of the physiological event in or on a person's body in three spatial dimensions;
    receiving a third input from the user identifying a time range of the physiological event;
    receiving a fourth input from the user identifying a quality of the physiological event;
    receiving a fifth input from the user identifying an administration of a medical treatment to the person;
    receiving a sixth input from the user identifying a configuration of the person's body associated with the physiological event; and
    rendering the physiological event and the administration of the medical treatment to the person on the avatar based on the first, second, third, fourth, fifth, and sixth inputs.

2. The method of claim 1, further comprising receiving a seventh input from the user identifying an action associated with the physiological event.

3. The method of claim 2, wherein the action associated with the physiological event is an action performed by the person.

4. The method of claim 2, wherein the action associated with the physiological event is an action done to the person.

5. The method of claim 1, wherein the quality of the physiological event comprises one or more of a nature of the physiological event or an intensity of the physiological event.

6. The method of claim 1, wherein the time range is a single point in time.

7. The method of claim 1, wherein the time range is a series of points in time.

8. The method of claim 1, wherein the physiological event is a somatic sensation of the person.

9. The method of claim 8, wherein the somatic sensation is pain.

10. The method of claim 1, wherein rendering the physiological event and the medical treatment on the avatar comprises generating a modified display for presentation to the user, the modified display comprising a modified avatar of the person's body in three spatial dimensions based on the first input, the second input, the third input, the fourth input, the fifth input, and the sixth input that illustrates the physiological event and the administration of the medical treatment to the person.

11. The method of claim 10, wherein the modified avatar of the person's body further illustrates the type of the physiological event, the time range of the physiological event, the quality of the physiological event, or any combination thereof.

12. The method of claim 10, wherein the modified avatar of the person's body further illustrates a configuration of the person's body during the physiological event.

13. The method of claim 10, wherein the modified avatar of the person's body further illustrates a particular anatomy of the person.

14. The method of claim 1, wherein rendering the physiological event on the avatar comprises generating and transmitting a data stream based on the first input, the second input, the third input, the fourth input, the fifth input, and the sixth input.

15. The method of claim 1, further comprising receiving a seventh input from the user identifying a particular anatomy of the person.

16. The method of claim 1, further comprising receiving a seventh input from the user requesting and causing the system to access and display information from a data store.

17. One or more computer-readable non-transitory storage media embodying instructions that are operable when executed to:
    generate a display for presentation to a user, the display comprising an avatar of a person's body in three spatial dimensions, the avatar being configured to receive one or more inputs from the user;
    receive a first input from the user identifying a type of a physiological event;
    receive a second input from the user identifying a location of the physiological event in or on a person's body in three spatial dimensions;
    receive a third input from the user identifying a time range of the physiological event;
    receive a fourth input from the user identifying a quality of the physiological event;
    receive a fifth input from the user identifying an administration of a medical treatment to the person;
    receive a sixth input from the user identifying a configuration of the person's body associated with the physiological event; and
    render the physiological event and the administration of the medical treatment to the person on the avatar based on the first, second, third, fourth, fifth, and sixth inputs.

18. The media of claim 14, the media embodying instructions that are further operable when executed to receive a seventh input from the user identifying an action associated with the physiological event.

19. The media of claim 18, wherein the action associated with the physiological event is an action performed by the person.

20. The media of claim 18, wherein the action associated with the physiological event is an action done to the person.

21. The media of claim 17, wherein the quality of the physiological event comprises one or more of a nature of the physiological event or an intensity of the physiological event.

22. The media of claim 17, wherein the time range is a single point in time.

23. The media of claim 17, wherein the time range is a series of points in time.

24. The media of claim 17, wherein the physiological event is a somatic sensation of the person.

25. The media of claim 24, wherein the somatic sensation is pain.

26. The media of claim 17, wherein rendering the physiological event and the medical treatment on the avatar comprises generating a modified display for presentation to the user, the modified display comprising a modified avatar of the person's body in three spatial dimensions based on the first input, the second input, the third input, the fourth input, the fifth input, and the sixth input that illustrates the physiological event and the administration of the medical treatment to the person.

27. The media of claim 17, wherein rendering the physiological event on the avatar comprises generating and transmitting a data stream based on the first input, the second input, the third input, the fourth input, the fifth input, and the sixth input.

28. An apparatus comprising: a memory comprising instructions executable by one or more processors; and one or more processors coupled to the memory and operable to execute the instructions, the one or more processors being operable when executing the instructions to:
    generate a display for presentation to a user, the display comprising an avatar of a person's body in three spatial dimensions, the avatar being configured to receive one or more inputs from the user;
    receive a first input from the user identifying a type of a physiological event;
    receive a second input from the user identifying a location of the physiological event in or on a person's body in three spatial dimensions;
    receive a third input from the user identifying a time range of the physiological event;
    receive a fourth input from the user identifying a quality of the physiological event;
    receive a fifth input from the user identifying an administration of a medical treatment to the person;
    receive a sixth input from the user identifying a configuration of the person's body associated with the physiological event; and
    render the physiological event and the administration of the medical treatment to the person on the avatar based on the first, second, third, fourth, fifth, and sixth inputs.

29. The apparatus of claim 28, wherein the quality of the physiological event comprises one or more of a nature of the physiological event or an intensity of the physiological event.

30. The apparatus of claim 28, wherein the time range is a single point in time.

31. The apparatus of claim 28, wherein the time range is a series of points in time.

32. The apparatus of claim 28, wherein the physiological event is a somatic sensation of the person.

33. The apparatus of claim 32, wherein the somatic sensation is pain.

34. The apparatus of claim 28, wherein rendering the physiological event and the medical treatment on the avatar comprises generating a modified display for presentation to the user, the modified display comprising a modified avatar of the person's body in three spatial dimensions based on the first input, the second input, the third input, the fourth input, the fifth input, and the sixth input that illustrates the physiological event and the medical treatment.

35. The apparatus of claim 28, wherein rendering the physiological event on the avatar comprises generating and transmitting a data stream based on the first input, the second input, the third input, the fourth input, the fifth input, and the sixth input.

* * * * *

UNITED STATES PATENT AND TRADEMARK OFFICE
CERTIFICATE OF CORRECTION

PATENT NO. : 8,928,671 B2
APPLICATION NO. : 12/954441
DATED : January 6, 2015
INVENTOR(S) : B. Thomas Adler et al.

Page 1 of 1

It is certified that error appears in the above-identified patent and that said Letters Patent is hereby corrected as shown below:

In the claims:

Col. 39, Ln. 42, Claim 18: After "the media of claim" and before "the media embodying instructions" delete "14," and insert -- 17, --.

Signed and Sealed this
Seventh Day of April, 2015

Michelle K. Lee
*Director of the United States Patent and Trademark Office*